US008916136B2

(12) United States Patent
Srivastava et al.

(10) Patent No.: US 8,916,136 B2
(45) Date of Patent: Dec. 23, 2014

(54) GLUCOSE BIOSENSOR SYSTEM COUPLED WITH AN ANTI-INFLAMMATORY MODULE AND METHODS FOR USING THE SAME

(75) Inventors: Rohit Srivastava, Mumbai (IN); Ayesha Chaudhary, Karnal (IN); Rahul Dev Jayant, Delhi (IN)

(73) Assignee: Indian Institute of Technology Bombay, Mumbai (IN)

( * ) Notice: Subject to any disclaimer, the term of this patent is extended or adjusted under 35 U.S.C. 154(b) by 685 days.

(21) Appl. No.: 12/819,868

(22) Filed: Jun. 21, 2010

(65) Prior Publication Data
US 2011/0262363 A1 Oct. 27, 2011

(30) Foreign Application Priority Data

Apr. 23, 2010 (IN) .......................... 1319/MUM/2010

(51) Int. Cl.
| | | |
|---|---|---|
| A61B 10/00 | (2006.01) | |
| A61K 8/00 | (2006.01) | |
| A61K 9/00 | (2006.01) | |
| A61K 49/00 | (2006.01) | |
| A61B 5/1459 | (2006.01) | |
| A61K 31/196 | (2006.01) | |
| A61K 31/573 | (2006.01) | |
| A61K 9/50 | (2006.01) | |
| A61B 5/145 | (2006.01) | |

(52) U.S. Cl.
CPC ......... *A61K 49/0091* (2013.01); *A61B 2562/16* (2013.01); *A61K 49/0054* (2013.01); *A61B 5/1459* (2013.01); *A61K 9/0024* (2013.01); *A61K 31/196* (2013.01); *A61K 49/0043* (2013.01); *A61K 31/573* (2013.01); *A61K 49/0056* (2013.01); *A61K 49/0041* (2013.01); *A61K 9/5036* (2013.01); *A61B 5/14532* (2013.01)
USPC ............................ 424/9.6; 424/400; 424/70.1

(58) Field of Classification Search
None
See application file for complete search history.

(56) References Cited

PUBLICATIONS

Levasalmi, J.M., et al., "Poly(4-methyl-1-pentene)-Supported Polyelectrolyte Multilayer Films: Preparation and Gas Permeability", 1997, Macromolecules, 30, pp. 1752-1757.*
Srivastava, R. et al., "Stabilization of glucose oxidase in alginate microspheres with photoreactive diazoresin nanofilm coatings," Biotechnology and Bioengineering, vol. 91, Issue 1, pp. 124-131, Jul. 5, 2005.
Abel P. U. et al., Biosensors for in vivo glucose measurement: can we cross the experimental stage Biosens. Bioelectron, 17(11-12): 1059-1070, 2002.
Abel P. U. et al., Biosensors for glycaemic control, *Sensor Reviews*, 21:297-304, 2001.
Brown, J.Q. et al., Encapsulation of glucose oxidase and an oxygen-quenched fluorophore in polyelectrolyte-coated calcium alginate microspheres as optical glucose sensor systems, *Biosens. Bioelectron.*, 2004, 5 pages.
Brown, J.Q. et al., Modeling of spherical fluorescent glucose microsensor systems: design of enzymatic smart tatoos, *Biosens. Bioelectron.*, 21(9):1760-1769, 2006.
Brown, J.Q. et al., Enzymatic fluorescent microsphere glucose sensors: evaluation of response under dynamic conditions, *Diabetes Technol. Ther.*, 8(3):288-295, 2006.
Caplin, N.J. et al., Subcutaneous glucose sensor values closely parallel blood glucose during insulin-induced hypoglycaemia, *Diabet. Med.* 20(3):238-241, 2003.
Chaudhary, A. et al., Glucose sensing using competitive binding assay co-encapsulated in uniform sized alginate microspheres, *Sens. Lett.*, 6:1-8, 2008.
Chinnayelka, S. et al., Microcapsule biosensors using competitive binding resonance energy transfer assays based on apoenzymes, *Anal. Chem.*, 77(17):5501-5511, 2005.
Chinnayelka, S. et al., Glucose sensors based on microcapsules containing an orange/red competitive binding resonance energy transfer assay, *Diabetes Technol. Ther.*, 8(3):269-278, 2006.
Chinnayelka, S. et al., Near-infrared resonance energy transfer glucose biosensors in hybrid microcapsule carriers, *J. Sens.*, 1-11, 2008.
Clark, L.C. et al., Long-term stability of electroenzymatic glucose sensors implanted in mice, *ASAIO Trans.*, 34(3):259-265, 1988.
Clark, L.C. et al., Implanted electroenzyrntic glucose sensors, *Diabetes Care*, 5(3):174-180, 1982.
Cote, G.L., Noninvasive and minimally-invasive optical monitoring technologies, *J. Nutr.*, 131(5):1596S-1604S, 2001.
D'Auria S. et al., Nanostructured silicon-based biosensors for the selective identification of analytes of social interest, *J. Phys.: Condens. Matter*, 18:S2019-S2028, 2006.
Freeland, A.C. Inference of blood glucose concentrations from subcutaneous glucose concentrations: applications to glucose biosensors, et al., *Ann. Biomed. Eng.*, 27(4):525-537, 1999.
Gross, T.M. et al., Efficacy and reliability of the continuous glucose monitoring system, *Diabetes Technol. Ther.*, 2 Suppl, 1:S19-26, 2000.
Heinemann, L. et al., Non-invasive continuous glucose monitoring in Type I diabetic patients with optical glucose sensors, *Diabetologia*, 41(7):848-854, 1998.
Hickey, T. et al., Dexamethasone/PLGA microspheres for continuous deliver of an anti-inflammatory drug for implantable medical devices, *Biomaterials*, 23(7):1649-1656, 2002.
McShane, M.J. et al., Optical system for implantable analyte sensors, *21st Annual International Conference of the IEEE-EMBS*, 2:804, 1999.

(Continued)

*Primary Examiner* — Michael G Hartley
*Assistant Examiner* — Lance Rider
(74) *Attorney, Agent, or Firm* — Foley & Lardner LLP

(57) ABSTRACT

Disclosed are apparatuses for detecting glucose levels in a subject. The apparatuses include a glucose sensor coupled with an anti-inflammatory module. The apparatus is configured to monitor blood glucose by detecting the fluorescence generated by the sensor and simultaneously reduce the tissue inflammation reaction. Also disclosed are biosensor systems including the apparatuses and methods of using the biosensor systems.

20 Claims, 10 Drawing Sheets

(56) References Cited

PUBLICATIONS

McShane, M.J. et al., Glucose monitoring using implanted fluorescent microspheres, *IEEE Eng. Med. Biol. Mag.*, 19:36-45, 2000.

McShane, M.J. et al., Monte Carlo modeling for implantable fluorescent analyte sensors, *IEEE Trans. Biomed. Eng.*, 47:624-632, 2000.

McShane, M.J,., Potential for glucose monitoring with nanoengineered fluorescent biosensors, *Diabetes Technol. Ther.*, 4(4):533-538, 2002.

Pauletto, N.S. et al., Nonsteroidal anti-inflammatory agents: potential modifiers of periodontal disease progression, *J. Can. Dent. Assoc.*, 63:824-829, 1997.

Pickup, J.C. et al., In vivo glucose monitoring: the clinical reality and the promise, *Biosens. Bioelectron.*, 20(10):1897-1902, 2005.

Pickup, J.C., Glucose sensors: present and future, *International Textbook of Diabetes Mellitus*, 3rd. ed., 1685-1694, 2004.

Ratner, B.D. et al., *Biomaterials Science: an introduction to materials in medicine*, 2nd ed., 2004, (Cover page and table of contents), 6 pages.

Robbins, S. L. et al., *Basic Pathology*, 6th ed., W.B. Saunders Company, 1997, (Cover page and table of contents), 4 pages.

Russell. R.J. et al., A fluorescence-based glucose biosensor using concanavalin A and dextran encapsulated in a poly)ethylene glycol) hydrogel, *Anal. Chem.*, 71(15):3126-3132, 1999.

Schultz, J.S. et al., Affinity sensors for individual metabolites, *Biotechnol. Bioeng. Symp.*, 9:65-71, 1979.

Schultz, J.S. et al., Affinity sensor: a new technique for developing implantable sensors for glucose and other metabolics, *Diabetes Care*, 5(3):245-253, 1982.

Sharkaway, A.A. et al., Engineering the tissue which encapsulates subcutaneous implants. III. Effective tissue response times, *J. Biomed. Mater. Res.*, 40:598-605, 1998.

Srinivasan, K.R. et al., Coupling of concanavalin A to cellulose hollow fibers for use in glucose affinity sensor, *Biotech. and Eng.*, XXVIII:233-239, 1986.

Thennadil, S.N. et al., Comparison of glucose concentration in interstitial fluid, and capillary and venous blood during rapid changes in blood glucose levels, *Diabetes Technol. Ther.*, 3(3):357-365, 2001.

Zhu, H. et al., Spontaneous loading of positively charged macromolecules into alginate-templated polyelectrolyte multilayer microcapsules, *Biomacromolecules*, 6(4),2221-2228, 2005.

Jayant, R.D. et al., Polyelectrolyte-coated alginate microspheres as drug deliver carriers for dexamethasone release, *Drug Delivery*, 16(6):331-340, 2009.

Chaudhary, A. et al., Evaluation of glucose sensitive affinity binding assay entrapped in fluorescent dissolved-core alginate microspheres, *Biotech. and Bioeng.*, 2009, 11 pages.

Chaudhary, A. et al., Glucose monitoring with nanoengineered fluorescent biosensors using glucose binding sensing elements, at The 8th Workshop on Biosensors and Bioanalytical Techniques in Environmental and Clinical Analysis, Oct. 3-6, 2007, Goa, India, 1 page.

Chaudhary, A. et al., Implantable nanoengineered glucose biosensors for continuous glucose sensing in diabetics, The 10th International Conference on Advanced Materials, IUMRS-ICAM 2007, Oct. 8-13, 2007, Bangalore, India, 1 page.

Jayant, R,D. et al.. Controlled release of anti-inflammatory agents using nanoengineered alginate microspheres: Towards and implantable glucose sensor, The 10th International Conference on Advanced Materials, IUMRS-ICAM 2007, Oct. 8-13, 2007, Bangalore, India, 1 page.

Jayant, R.D. et al., Dexamethasone release from uniform sized nanoegineered alginate microspheres, The XV International workshop on Bioencapsulation in Vienna, Austria from Sep. 6-8, 2007, 1 page.

Jayant, R.D. et al., Alginate rnicrospheres as drug delivery carriers for localized inflammation control, The 10th International Conference on Advanced Materials, IUMRS-ICAM 2007, Oct. 8-13, 2007, Bangalore, India, 1 page.

Jayant, R.D. et al., Dexamethasone release from uniform sized nanoengineered alginate microspheres, *J. Biomed. Nanotechnol.*, 3(3):1-9, 2007.

Ballerstadt, R. et al., A fluorescence affinity hollow fiber sensor for continuous transdermal glucose monitoring, *Anal. Chem.*, 72:4185-4192, 2000.

Chaudhary, A. et al., Dissolved core alginate microspheres as "smart-tattoo" glucose sensors, *Conf Proc IEEE Eng Med Biol Soc*, 2009:4098-101, Sep. 2009.

Sharkawy, A.A. et al., Engineering the tissue which encapsulates subcutaneous implants. II. Plasma-tissue exchange properties, NSF Center for Emeraing Cardiovascular Technology, Department of Biomedical Engineering, Duke University, Durham, North Carolina, 1997, pp. 586-597.

Pickup, J. et al., In vivo glucose sensing for diabetes management: progress towards non-invasive monitoring, *BMI*, 319, 1999, pp. 1-4.

Chinnayelka, S. et al., Resonance energy transfer nanobiosensors based on affinity binding between apo-enzyme and its substrate, *Biomacromolecules*, 5:1657-1661, 2004.

McShane, M.J. et al., Microcapsules as "smart tattoo" glucose sensors: Engineering systems with enzymes and glucose-binding sensing elements, *Topics in Fluorescence*, vol. 10., 43 pages, 2006.

Srivastava, et al., "Application of self-assembled ultra-thin film coatings to stablize macromolecule encapsulation in alginate microspheres", Journal of Microencapsulation, (2005), vol. 22, No. 4, pp. 397-411, Taylor & Francis.

Srivastava, et al., "Stable Encapsulation of Active Enzyme by Application of Multilayer Nanofilm Coatings to Alginate Microspheres", Macromolecular Bioscience, (2005), vol. 5, No. 8, pp. 717-727, Wiley-VCH Verlag.

Svensson, et al., "Monoclonal Antibody-beta-Lactamase Conjugates for the Activation of a Cephalosporin Mustard Prodrug", Bioconjugate Chemistry, (1992), vol. 3, No. 2, pp. 176-181, American Chemical Society.

Swoboda, B.E.P., "The Relationship Between Molecular Conformation and the Binding of Flavin-Adenine Dinucleotide in Glucose Oxidase", Biochimica et Biophysica Acta, (1969), vol. 175, pp. 365-379.

\* cited by examiner

8A -ve Control (Plain skin)

8B 7 Day (10X)

8C 14 Day (10X)

8D 21 Day (40X)

8E 30 Day (40X)

9A -ve Control (Plain skin)

9B 7 Day

9C 14 Day

9D 21 Day

9E 30 Day

GLUCOSE BIOSENSOR SYSTEM COUPLED WITH AN ANTI-INFLAMMATORY MODULE AND METHODS FOR USING THE SAME

CROSS-REFERENCE TO RELATED APPLICATION

This application claims priority to India Patent Application No. 1319/MUM/2010, filed Apr. 23, 2010, the entire contents of which are incorporated by reference herein and for all purposes as if fully set forth herein.

TECHNICAL FIELD

The present technology relates generally to the fields of implantable biosensors and disease diagnosis and monitoring, including the diagnosis and monitoring of diabetes.

BACKGROUND

The following description is provided to assist the understanding of the reader. None of the information provided or references cited is admitted to be prior art.

Diabetes is the major cause of long term tissue complications (hypoglycemia and hyperglycemia) affecting both the small and large blood vessels. The myriad of complications arising due to diabetes require painful monitoring of glucose levels inside the body because of the harmful impact of fluctuations of glucose levels on the body. Therefore, it is required to monitor the glucose levels continuously.

While some glucose biosensors have been developed and are available commercially, they are not so commonly used by the diabetes patients because of associated drawbacks, including skin irritation, low precision and inaccuracy. Furthermore, many devices require a 3 h warm-up period and calibration each time before use. Therefore, most diabetes patients prefer to measure their blood glucose using a glucometer, which additionally involves pain. As a result, there is poor patient compliance with recommended testing regimens due to the invasive nature of glucose monitoring in blood, primarily undertaken by "finger-pricking."

SUMMARY

Provided herein are methods and apparatuses for the detection and monitoring of glucose, which may be useful for, inter alia, the diagnosis and monitoring of diabetes and related ailments. Accordingly, in one aspect, a nanoengineered implantable glucose sensor is provided, the sensor comprising: a population of alginate microspheres loaded with one or more anti-inflammatory agents, wherein the population is a mixture of uncoated and polyelectrolyte-coated alginate microspheres; and a population of dissolved core alginate microspheres incorporating one or more fluorophore-labeled glucose binding agents and one or more fluorophore-labeled glucose analogues. In some embodiments, the fluorophore on the one or more fluorophore-labeled glucose binding agents and the fluorophore on the one or more fluorophore labeled glucose analogues form a Fluorescence Resonance Energy Transfer (FRET) pair. In an illustrative embodiment, the FRET pair is a visible dye FRET pair or a near infrared FRET pair.

In one embodiment, the alginate microspheres loaded with the one or more anti-inflammatory agents have an average diameter from about 20 μm to about 100 μm. In some embodiments, the alginate microspheres loaded with the one or more anti-inflammatory agents have an average diameter of about 60 μm.

In some embodiments, the dissolved core alginate microspheres incorporating the one or more fluorophore-labeled glucose binding agents have an average diameter from about 5 μm to about 100 μm. In other embodiments, the dissolved core alginate microspheres incorporating the one or more first fluorophore-labeled glucose binding agents and the one or more second fluorophore-labeled glucose analogues have an average diameter of about 10 μm to about 20 μm.

In one embodiment, the population of alginate microspheres loaded with the one or more anti-inflammatory agents comprise from about 25% to about 90% polyelectrolyte coated microspheres. In some embodiments, the population of alginate microspheres loaded with the one or more anti-inflammatory agents comprise about 75% polyelectrolyte coated microspheres and about 25% uncoated microspheres. In some embodiments, the population of alginate microspheres loaded with the one or more anti-inflammatory agents comprise about 50% polyelectrolyte coated microspheres and about 50% uncoated microspheres. In some embodiments, the population of alginate microspheres loaded with the one or more anti-inflammatory agents comprise about 25% polyelectrolyte coated microspheres and about 75% uncoated microspheres.

In some embodiments, the one or more glucose binding agents are selected from the group consisting of: apo-glucose oxidase, Concanavalin A, and glucose binding protein. In one embodiment, the one or more fluorophore-labeled glucose binding agents is a fluorophore-labeled apo-glucose oxidase. In some embodiments, the one or more fluorophore-labeled glucose binding agents is a visible fluorophore or a near infrared fluorophore-labeled apo-glucose oxidase. In an illustrative embodiment, the one or more fluorophore-labeled glucose binding agents is a Tetramethyl Rhodamine Isothiocyanate (TRITC) or a QSY-21-tagged apo-glucose oxidase.

In some embodiments, the glucose analogue is selected from the group consisting of dextran amino, dextran, and β-cyclodextrin. In some embodiments, the glucose analogue is a visible fluorophore labeled dextran or a near infrared fluorophore-labeled dextran amino. In some embodiments, the glucose analogue is a Fluorescein isothiocyanate (FITC) labeled dextran or an Alexa Fluor-647-labeled dextran amino. In an illustrative embodiment, the TRITC tagged apo-glucose oxidase is bound to FITC-dextran or QSY-21-tagged apo-glucose oxidase is bound to AF-647-dextran amino in the absence of glucose.

In one embodiment, the one or more anti-inflammatory agents are selected from the group consisting of: dexamethasone, hydrocortisone, cortisone acetate, prednisone, prednisolone, methylprednisolone, betamethasone, triamcinolone, diclofenac, ibuprofen, naproxen, and celecoxib. In an illustrative embodiment, the one or more anti-inflammatory agents is dexamethasone disodium salt or diclofenac sodium salt.

In one embodiment, the polyelectrolyte-coated alginate microspheres comprise at least one bilayer of a polycation and a polyanion. In some embodiments, the polycation is selected from the group consisting of: poly(allylamine hydrochloride) (PAH) and poly(diallyldimethylammonium chloride) (PDDA). In other embodiments, the polyanion is selected from the group consisting of: poly(styrene sulfonate) (PSS) and poly(acrylic acid) (PAA). In an illustrative embodiment, the at least one bilayer comprises a polyelectrolyte pair selected from the group consisting of: PAH/PSS, PDDA/PSS, PAH/PAA and cross-linked PAA/PAH.

In one embodiment, the polyelectrolyte-coated alginate microspheres comprise one bilayer of a polycation and a polyanion. In some embodiments, the polyelectrolyte-coated alginate microspheres comprise two bilayers of a polycation and a polyanion. In other embodiments, the dissolved core alginate microspheres incorporating the one or more fluorophore-labeled glucose binding agents are coated with a polyelectrolyte.

In one embodiment, the alginate microspheres loaded with the one or more anti-inflammatory agents comprise from about 25% to about 90% by weight of the implantable glucose sensor and the dissolved core alginate microspheres incorporating the one or more fluorophore-labeled glucose binding agents comprise from about 50% to about 80% by weight of the implantable glucose sensor.

In one embodiment, the dissolved core alginate microspheres further comprise a near-infra red reference fluorophore in a polyelectrolyte coating. In some embodiments, the reference fluorophore is AF-750 tagged to a PAH polyelectrolyte.

In one aspect, the present technology provides a method for monitoring the blood glucose of a subject, the method comprising: detecting a fluorescence emission from an implanted glucose sensor, wherein the implanted glucose sensor comprises a population of alginate microspheres loaded with one or more anti-inflammatory agents, wherein the population is a mixture of uncoated and polyelectrolyte-coated alginate microspheres; and a population of dissolved core alginate microspheres incorporating one or more fluorophore-labeled glucose binding agents and one or more fluorophore-labeled glucose analogues, wherein the change in intensity of the fluorescence emission compared to a reference fluorescence is correlated to the blood glucose level of the subject.

In one embodiment of the method the one or more fluorophore-labeled glucose binding agents is a TRITC-tagged or QSY-21-tagged apo-glucose oxidase. In some embodiments, the TRITC-tagged apo-glucose oxidase is bound to FITC-dextran in the absence of glucose and there is energy transfer from FITC to TRITC. In some embodiments, the QSY-21-tagged apo-glucose oxidase is bound to AF-647-dextran amino in the absence of glucose and the fluorescence of AF-647 is quenched.

In one embodiment, the dissolved core alginate microspheres further comprise a reference fluorophore in a polyelectrolyte coating. In some embodiments, the reference fluorophore is AF-750. In one embodiment, the method further comprises detecting the fluorescence emission of the reference fluorophore. In some embodiments, the ratio of the fluorescence emission from the one or more fluorophore-labeled glucose analogue compared to the fluorescence emission from the one or more fluorophore-labeled glucose binding agents is correlated to the blood glucose level of the subject. In other embodiments, the ratio of the fluorescence emission from the one or more fluorophore-labeled glucose binding agents compared to the fluorescence emission of the reference fluorophore is correlated to the blood glucose level of the subject.

In another aspect, the present technology provides a kit for monitoring the blood glucose of a subject, the kit comprising: a population of alginate microspheres loaded with one or more anti-inflammatory agents, wherein the population is a mixture of uncoated and polyelectrolyte-coated alginate microspheres; a population of dissolved core alginate microspheres incorporating one or more fluorophore-labeled glucose binding agents and one or more fluorophore-labeled glucose analogues; and optical instrumentation for detecting fluorescence emission from the one or more fluorophore-labeled glucose binding agents.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
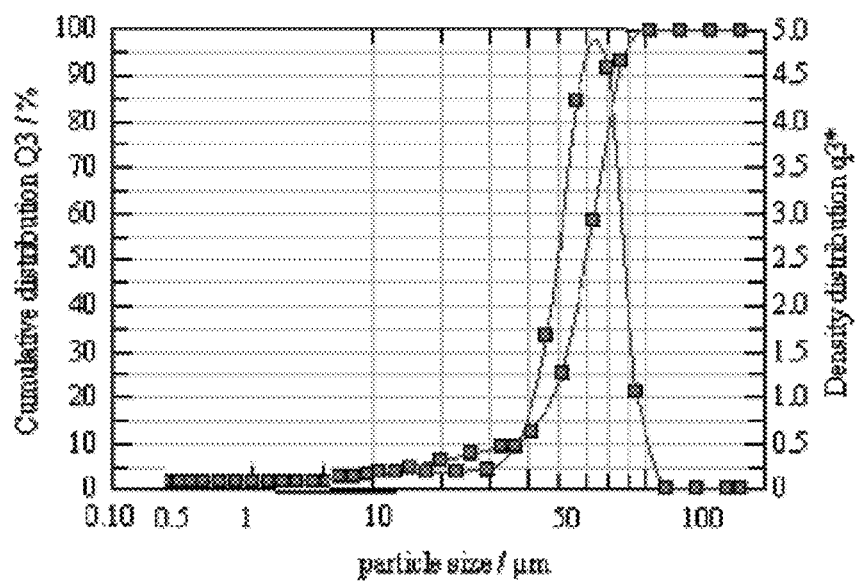
FIG. 1 is a graph of an illustrative particle size distribution of calcium alginate microspheres prepared using commercially available droplet generator.

In the following detailed description, reference is made to the accompanying figures which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the "administration" of an agent, drug, or peptide to a subject includes any route of introducing or delivering to a subject a compound to perform its intended function. Administration can be carried out by any suitable route, including intraocularly, orally, intranasally, parenterally (intravenously, intramuscularly, intraperitoneally, or subcutaneously), or topically. Administration includes self-administration and the administration by another.

As used herein, the term "effective amount" refers to a quantity sufficient to achieve a desired therapeutic and/or prophylactic effect, e.g., an amount which results in the prevention of, or a decrease in, the symptoms associated with a condition. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

The term "transport," as in the "transport" of a compound of interest across a body tissue, refers to passage of the compound in the direction of external to internal movement.

The terms "controlled release" or "sustained release" refers to the release of a given drug from a device at a predetermined rate. Such rate of release can be zero order, pseudo-zero order, first order, pseudo-first order, and the like. Thus, relatively constant or predictably varying amounts of the drug can be delivered over a specified period of time.

The terms "drug," "compound," "active agent," "actives," "pharmaceutical composition," "pharmaceutical formulation," and "pharmacologically active agent" are used interchangeably herein to refer to any chemical compound, complex or composition, charged or uncharged, that is suitable for administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

The terms "optional" and "optionally" mean that the subsequently described circumstance may or may not occur, so that the description includes instances where the circumstance occurs and instances where it does not.

By "subject," it is meant any animal, including mammals, e.g., a human, a primate, a dog, a cat, a horse, a cow, a pig, or a rodent, e.g., a rat or mouse. In some such embodiments, the subject is a human. The subjects include any animal that can benefit from the administration of the disclosed devices. The subjects may be normal, healthy subjects or subjects having, or at risk for developing, a particular biological disease or condition. By way of example only, the subject may be a subject having, or at risk for developing, high blood glucose levels, i.e., diabetes. The term "patient" refers to a "subject" who is, or is suspected to be, afflicted with diabetes.

Disclosed herein are devices and methods for detecting the presence or absence and levels of glucose in subjects based, at least in part, on results generated by using the testing methods described herein. Further disclosed herein are methods for monitoring the status of subjects diagnosed with diabetes based at least partially on results of tests on a sample. This disclosure is drawn, inter alia, to methods of diagnosing and monitoring diabetes. Also provided herein are apparatuses and kits for detecting glucose levels, biosensor systems including such apparatuses, and methods of using the biosensor systems.

Monitoring of blood glucose levels on a regular basis and analyzing the results is an integral part of managing diabetes. Of the many known glucose monitors, continuous glucose monitoring (CGM) systems are known for their efficiency and for providing a comprehensive glycemic trend in a subject. CGMS are comprised of a tiny glucose-sensing device called a "sensor" which is inserted just under the skin of a subject. The sensor measures the level of glucose in the tissue at short time intervals and sends the information via a wire to a device called a "monitor." The system automatically records an average glucose value every 5 minutes for up to 72 h. CGMS are frequently associated with disadvantages such as inflammation, infection, pain and immune reactions caused by long-term use of the device.

At least one problem associated with implantable glucose sensors is the inflammatory response of the body to tissue on implantation. The inflammatory response consists of several phases viz acute, chronic, and fibrotic encapsulation. The acute inflammatory reaction start within 24-48 h after the implantation and this later on will lead to a chronic inflammatory reaction which continues for 2-3 weeks, after which the fibrotic tissue is deposited around the sensor or implant or after this period body starts its normal tissue regrowth. So, to maintain the functionality and longevity of the implanted sensor, it is desirable that the inflammation response be curbed. The present glucose sensor would be a significant improvement as it effectively addresses the problem of inflammation associated with implantable glucose sensors.

Glucose Sensor

In one aspect, the present disclosure provides a nanoengineered implantable glucose, wherein the sensor includes: a population of alginate microspheres loaded with one or more anti-inflammatory agents, wherein the population is a mixture of uncoated and polyelectrolyte-coated alginate microspheres; and a population of dissolved core alginate microspheres incorporating one or more labeled glucose binding agents and one or more labeled glucose analogues.

The term "microspheres" as used herein includes spherical colloidal structures, e.g., formed from biocompatible polymers such as subject compositions, having a size ranging from about 1 μm to about 1000 μm. These microspheres also include microparticles, microcapsules, as well as structures that may not be readily placed into either of the above categories, all with dimensions on average of less than about 1000 μm. In certain embodiments, the microspheres have an average diameter of about 500, 200, 100, 50 or 10 μm. A composition having microspheres may include particles of a range of particle sizes. In certain embodiments, the particle size distribution may be uniform, e.g., within less than about a 50%, within less than about a 40%, within less than about a 30%, within less than about a 20% or within less than about a 10% standard deviation of the median volume diameter.

In some embodiments, the alginate microspheres loaded with the one or more anti-inflammatory agents have an average diameter from about 1 μm to about 500 μm. In some embodiments, the alginate microspheres loaded with the one or more anti-inflammatory agents have an average diameter from about 20 μm to about 100 μm. In some embodiments, the alginate microspheres loaded with the one or more anti-inflammatory agents have an average diameter from about 30 μm to about 80 μm. In an illustrative embodiment, the alginate microspheres loaded with the one or more anti-inflammatory agents have an average diameter of about 60 μm.

In some embodiments, the nanoengineered alginate microspheres are partially dissolved from inside to create free space within the microspheres to allow displacement of the NIR sensing assay during competitive binding reaction; wherein dissolution of core is performed by using 0.1 M sodium citrate Tris HCl solution, or chelating agents such as ethylene glycol-bis(β-aminoethyl ether)-N,N,N',N'-tetracetic acid (EGTA), ethylenediaminetetraacetic acid disodium salt dihydrate (EDTA), lactate and phosphate, or by a high concentration of ions such as $Na^+$ or $Mg^{2+}$. In some embodiments, the dissolved core alginate microspheres incorporating the one or more fluorophore-labeled glucose binding agents have an average diameter from about 1 μm to about 500 μm. In some embodiments, the dissolved core alginate microspheres incorporating the one or more fluorophore-labeled glucose binding agents have an average diameter from about 5 μm to about 100 μm. In an illustrative embodiment, the dissolved core alginate microspheres incorporating the one or more fluorophore-labeled glucose binding agents have an average diameter of about 10 μm to about 20 μm.

The population of each type of microsphere in the sensor may vary depending on several factors. For example, the ratio of uncoated versus polyelectrolyte coated microspheres depends upon the desired drug release profile. Thus, in one embodiment, the population of alginate microspheres loaded with the one or more anti-inflammatory agents may include from about 0% to about 100% polyelectrolyte coated microspheres. In some embodiments, the population of alginate microspheres loaded with the one or more anti-inflammatory agents may include from about 25% to about 90% polyelectrolyte coated microspheres. In one embodiment, the population of alginate microspheres loaded with the one or more anti-inflammatory agents include from about 60% to about 90% polyelectrolyte coated microspheres. In some embodiments, the population of alginate microspheres loaded with the one or more anti-inflammatory agents include about 75% polyelectrolyte coated microspheres and about 25% uncoated microspheres. In other embodiments, the population of alginate microspheres loaded with the one or more anti-inflammatory agents include about 50% polyelectrolyte coated microspheres and about 50% uncoated microspheres. In some embodiments, the population of alginate microspheres loaded with the one or more anti-inflammatory agents include about 25% polyelectrolyte coated microspheres and about 75% uncoated microspheres.

The function of the glucose sensor system is based on competitive binding and fluorescence resonance energy transfer (FRET). The system includes one or more fluorophore-labeled glucose binding agents and one or more fluorophore-labeled glucose analogues. The one or more fluorophore-labeled glucose binding agents and the fluorophore on the one or more fluorophore-labeled glucose analogues form a FRET pair. A number of combination of FRET pairs can be used depending on the biological applications. Based on their emission characteristics, the FRET pair can be a visible dye FRET pair or a near infrared FRET pair.

The fluorophore-system may include a donor fluorophore and an acceptor dye. In the absence of glucose, when donor fluorophore is bound to acceptor fluorophore, there is energy transfer from donor to acceptor fluorophore, whereby fluorescence of donor fluorophore is quenched. When glucose is introduced into the system, it displaces one or more fluorophore-labeled glucose analogues, resulting in an increase in the donor fluorophore fluorescence. The change in donor fluorophore fluorescence is correlated to the variation in glucose levels. Any suitable glucose binding agents known in the art may be used in the glucose sensor. In some embodiments, the glucose binding agent is selected from the group consisting of: apo-glucose oxidase, Concanavalin A, and glucose binding protein. In some embodiments, the one or more fluorophore-labeled glucose binding agents can be a visible fluorophore or a near infrared fluorophore-labeled apo-glucose oxidase.

In one embodiment, the one or more fluorophore-labeled glucose binding agents is a fluorophore-labeled apo-glucose oxidase. Suitable acceptor dyes which can be used are quencher acceptor dyes and include those which have broad absorption wavelengths and serve as quenchers of fluorescence emission. In some embodiments, the acceptor dye is a non-fluorescent dye selected from QSY-21, QSY-7, QSY-9, QSY-33, QSY-35, DABCYL, BHQ™-1, BHQ™-2, Iowa Black™ FQ/RQ and the like, or a visible dye selected from TRITC, N,N,N',N'-tetramethyl-6-carboxyrhodamine (TAMRA) and 6-carboxy-X-rhodamine (ROX). In other embodiments, the acceptor dye is a fluorescent dye selected AF-488, AF-546, AF-555, AF-568, AF-594, AF-610, AF-647, AF-680, AF-700, AF-750, and the like. Suitable fluorescent donor dyes are those which can be used for fluoroimmunoassays and which span the visible and infrared spectrum and match the principal output wavelengths of common excitation sources. In some embodiments, the donor dye is Fluorescein isothiocyanate (FITC). In some embodiments, the donor dye is selected from the Alexa Fluor series of dyes such as, e.g., AF-350, AF-405, AF-430, AF-488, AF-514, AF-532, AF-546, AF-555, AF-568, AF-594, AF-610, AF-633, AF-635, AF-647, AF-660, AF-680, AF-700, AF-750 and AF-790, and other dyes such as, e.g., R-phycoerythrin, Allophycocyanin, 6-FAM™, Rhodamine Red®-X, Rhodamine Green™-X, Oregon Green™ 514, TET™, JOE, HEX™, Cy3™, Cy5™ TAMRA™, ROX™, Texas Red™-X, Bodipy 630/650™-X, Bodipy 650/66, and the like. In illustrative embodiments, AF-647 is used as donor dye and QSY-21 is used as an acceptor. QSY-21 possesses a broad and intense absorption maximum (661 nm) but no fluorescence, thereby preventing any background signal, hence making it useful as an acceptor.

Alternatively, a visible light dye system comprising dyes such as, e.g., fluorescein isothiocyanate (FITC)-dextran (FD) and tetramethylrhodamine isothio-cyanate (TRITC)-AG can be used to detect fluorescence. A fluorescence spectrum of the dissolved-core alginate microspheres loaded with the FD/TRITC-Con A or FD/TRITC-apo-glucose oxidase complex dispersed in DI water/simulated interstitial fluid is collected as the starting point by exciting sample at 488 nm. Fluorescence spectra is then collected after each addition of 3 mm to 60 mm β-D glucose solution to the microspheres. Sensitivity curves are obtained by calculating the % change in FITC/TRITC peak ratio versus glucose concentration. Thus, in an illustrative embodiment, the one or more fluorophore-labeled glucose binding agents is a TRITC or a QSY-21-tagged apo-glucose oxidase.

In some embodiments, the glucose analogue is selected from the group consisting of dextran amino, dextran, and β-cyclodextrin. In some embodiments, the glucose analogue is a visible fluorophore labeled dextran or a near infrared fluorophore-labeled dextran amino. In some embodiments, the glucose analogue is a FITC labeled dextran or an Alexa Fluor-647-labeled dextran amino. In some embodiments, the TRITC tagged apo-glucose oxidase is bound to FITC-dextran. In some embodiments, the QSY-21-tagged apo-glucose oxidase is bound to AF-647-dextran amino in the absence of glucose.

The glucose sensor is designed to effectively address the problem of inflammation associated with implantable devices. The present glucose sensor, therefore, includes a population of alginate microspheres loaded with one or more anti-inflammatory agents. The anti-inflammatory agent may be any anti-inflammatory drug known in the art which can prevent or suppress inflammatory conditions substantially without side effects. Such anti-inflammatory drugs include, e.g., steroidal, non-steroidal and naturally occurring anti-inflammatory agents. Exemplary anti-inflammatory agents include hydrocortisone, dexamethasone, cortisone acetate, prednisone, prednisolone, methylprednisolone, betametasone, trimcinolone, diclofenac, ibuprofen, naproxen, celecoxib, loteprednol, fluocinolone, medrysone, fluorometholone, and salts and derivatives thereof. In one embodiment, the one or more anti-inflammatory agents are selected from the group consisting of: hydrocortisone, dexamethasone, cortisone acetate, prednisone, prednisolone, methylprednisolone, betametasone, trimcinolone, diclofenac, ibuprofen, naproxen, and celecoxib, or combinations thereof. In some embodiments, the one or more anti-inflammatory agents is dexamethasone. In an illustrative embodiment, the one or more anti-inflammatory agents is dexamethasone disodium salt or diclofenac sodium salt.

Concentrations of anti-inflammatories in the glucose sensor may range from about 0.001 to about 10.0 percent by weight, from about 0.01 to about 5.0 percent by weight, and in illustrative embodiments, from about 0.02 to about 2.0 percent by weight. Accordingly, based on the desired therapeutic effect, the distribution of the alginate microspheres loaded with the one or more anti-inflammatory agents and the dissolved core alginate microspheres incorporating the one or more fluorophore-labeled glucose binding agents can be optimized. Thus, in one embodiment, the alginate microspheres loaded with the one or more anti-inflammatory agents include from about 1% to about 100% by weight of the implantable glucose sensor, and the dissolved core alginate microspheres incorporating the one or more fluorophore-labeled glucose binding agents include from about 20% to about 90% by weight of the implantable glucose sensor. In an illustrative embodiment, the alginate microspheres loaded with the one or more anti-inflammatory agents include from about 25% to about 90% by weight of the implantable glucose sensor, and the dissolved core alginate microspheres incorporating the one or more fluorophore-labeled glucose binding agents include from about 50% to about 80% by weight of the implantable glucose sensor.

In some embodiments, the dissolved core alginate microspheres incorporating the one or more fluorophore-labeled glucose binding agents are coated with a polyelectrolyte. The polyelectrolyte coating may be a single layer or multilayer coating. In one embodiment, the polyelectrolyte-coated alginate microspheres include a single or multiple bilayer of a polycation and a polyanion. In some embodiments, the polyelectrolyte-coated alginate microspheres include at least one bilayer of a polycation and a polyanion. In some embodiments, the polyelectrolyte-coated alginate microspheres include one bilayer of a polycation and a polyanion. In other embodiments, the polyelectrolyte-coated alginate microspheres include two bilayers of a polycation and a polyanion.

Suitable polycations and polyanions known in the art can be used to form the polyelectrolyte coating. This coating can be deposited according to the layer-by-layer (LBL) deposition technique known in the art. Exemplary polycations which can be used include poly(diallyldimethylammonium chloride) (PDDA), poly(allylamine hydrochloride) (PAH), polyethylene imine (PEI), poly(L-lysine) (PLL), poly(dimethylaminoethyl acrylamide) (DAEA) and modified chitosan. Exemplary polyanions which can be used include poly (acrylic acid) (PAA), poly(styrene sulfonate) (PSS), and (poly[1-[4-(3-carboxy-4-hydroxy-phenylazo)benzene sulfonamido]-1,2-ethanediyl, sodium salt]) (PAZO). In some embodiments, natural polyelectrolytes such as chondroitin sulfate (CS), hyaluronic acid (HA), heparan sulfate (HS) and polycarboxylic acid (PCA) are employed. In some embodiments, the polycation is selected from the group consisting of: poly(allylamine hydrochloride) (PAH), and poly(diallyldimethylammonium chloride) (PDDA). In other embodiments, the polyanion is selected from the group consisting of: poly (styrene sulfonate) (PSS) and poly(acrylic acid) (PAA). Any cationic-anionic polyelectrolyte pairs are appropriate to form the polyelectrolyte layers if one of the polyelectrolyte is a strong electrolyte and the other is weak, and in addition, the pharmaceutical use of which is permitted. In some embodiments, the polyelectrolyte pair is selected from PAH/PSS, PAA/PAH, PDDA/PSS, CS/DAEA, HA/PLL, PEI/PSS, Chitosan/PSS, PDDA/PVS, PEI/PAA, crosslinked-PAA/PAH, PDAC/PVS, and PDAC/PAS. In some embodiments, bi- or multi-functional compounds can be used to crosslink the polymers. For example, 1-ethyl-3-(3-dimethylaminopropyl) carbodiimide (EDC) and N-hydroxysulfosuccinimide (NHSS) can be used to crosslink PAA and PAH. In an illustrative embodiment, the at least one bilayer includes a polyelectrolyte pair selected from the group consisting of: PAH/PSS, PDDA/PSS, PAH/PAA and cross-linked PAA/PAH.

In one embodiment of the method, the dissolved core alginate microspheres further includes a reference fluorophore. The reference fluorophore can be incorporated within the polyelectrolyte nanofilms around the dissolved core alginate microspheres. The fluorescence of the reference dye remains constant at all times and it acts as a reference fluorophore for ratiometric monitoring. Any suitable dye, other than the donor dye to be used, such as other donor dyes described above, can serve as a reference dye. In an illustrative embodiment, the reference dye is AF-750. In some embodiments, the AF-750 is tagged to a PAH polyelectrolyte. AF-750 is weakly excited at about 640 nm when the donor dye AF-647 is strongly excited, but unlike AF-647, it is not quenched by QSY-21.

Although alginate is mentioned as a suitable biodegradable polymer matrix for the microspheres because of its high stability towards mechanical stress and high encapsulation capacity, other suitable polymer matrices can also be employed as microsphere matrices for the sensors. In illustrative embodiments, polymer matrices include polymeric substrates such as Poly Ortho Ester, poly(trimethylene carbonate) (PTMC) and Tri(ethylene glycol) methyl ether (mPEG3)-PTMC11, poly(lactic-co-glycolic acid) (PLGA), porous PLGA, starch-microparticles, PLGA microsphere and poly(vinyl alcohol) hydrogel, PLGA and poly(lactic acid) nanoparticles, alginate hydrogels, polyethylene, oligo(poly(ethylene glycol) fumarate), poly(caprolactone), poly(ethylene oxide), poly(dimethyl siloxane), and polyurethane. Alginate used herein can be in its various salt forms such as, e.g., sodium alginate, calcium alginate, potassium alginate, magnesium alginate and ammonium alginate. Manganese carbonate and silica-alginate can also be used as dissolved core microspheres. In illustrative embodiments, calcium alginate or sodium alginate is used as the matrix for the drug-loaded microspheres and the dissolved core for other microspheres.

Methods

The disclosed biosensor systems may be used in a variety of applications. In one aspect, a method for monitoring the blood glucose of a subject using the implanted glucose sensor is provided. Thus, in one embodiment, the present technology provides a method for monitoring the blood glucose of a subject, the method comprising: detecting a fluorescence emission from an implanted glucose sensor, wherein the implanted glucose sensor includes a population of alginate microspheres loaded with one or more anti-inflammatory agents, wherein the population is a mixture of uncoated and polyelectrolyte-coated alginate microspheres; and a population of dissolved core alginate microspheres incorporating one or more fluorophore-labeled glucose binding agents and one or more fluorophore-labeled glucose analogues, wherein the intensity of the fluorescence emission is correlated to the blood glucose level of the subject.

In one embodiment of the method, the one or more fluorophore-labeled glucose binding agents is a TRITC-tagged or a QSY-21-tagged apo-glucose oxidase. In some embodiments, the TRITC-tagged apo-glucose oxidase is bound to FITC-dextran in the absence of glucose and there is energy transfer from FITC to TRITC. In other embodiments, the QSY-21-tagged apo-glucose oxidase is bound to AF-647-dextran amino in the absence of glucose and the fluorescence of AF-647 is quenched.

In one embodiment of the method, the dissolved core alginate microspheres further include a reference fluorophore. Any suitable fluorophore, other than the donor fluorophore can be used, such as other donor dyes described above. In an illustrative embodiment, the reference fluorophore is AF-750. The reference fluorophore can be incorporated within the polyelectrolyte nanofilms around the dissolved core alginate microspheres. The fluorescence of the reference fluorophore remains constant at all times. It acts as a reference fluorophore for ratiometric monitoring and, therefore, decreases the sensitivity to noise and fluctuations in the sensor properties. Therefore, in one embodiment, the method further includes detecting the fluorescence emission of the reference fluorophore. In some embodiments, the ratio of the fluorescence emission from the one or more fluorophore-labeled glucose analogue compared to the fluorescence emission from the one or more fluorophore-labeled glucose binding agents is correlated to the blood glucose level of the subject. In other embodiments, the ratio of the fluorescence emission from the one or more fluorophore-labeled glucose binding agents compared to the fluorescence emission of the reference fluorophore is correlated to the blood glucose level of the subject.

The transdermally implanted glucose sensors are interrogated non-invasively using simple optical instrumentation which can detect fluorescence. The sensor is designed to take multiple readings along with the anti-inflammatory module which keeps the sensor functional.

Kits

For the convenience of the patient or treating physician, the glucose formulation can be provided in a kit containing all necessary equipment (e.g., vials comprising alginate microspheres loaded with one or more anti-inflammatory agents and dissolved core alginate microspheres incorporating one or more fluorophore-labeled glucose binding agents, optical instrumentation for florescence detection, syringes, needles, etc.) for a specific treatment or detection course (e.g., 30 days).

Thus, in yet another aspect, the present technology provides a kit for monitoring the blood glucose of a subject, wherein the kit includes: a population of alginate microspheres loaded with one or more anti-inflammatory agents, wherein the population is a mixture of uncoated and polyelectrolyte-coated alginate microspheres; a population of dissolved core alginate microspheres incorporating one or more fluorophore-labeled glucose binding agents and one or more fluorophore-labeled glucose analogues; and optical instrumentation for detecting fluorescence emission from the one or more fluorophore-labeled glucose binding agents.

The glucose sensors can be implanted or delivered to the desired site in the subject's body using various techniques known in the art. Some of the techniques used include, e.g., intramuscular or hypodermal delivery and micro-needle based implantation technique. In some embodiments, the alginate microspheres dispersed in vehicle are injected subcutaneously using needles of suitable gauge size.

The present technology, thus generally described, will be understood more readily by reference to the following examples, which are provided by way of illustration and are not intended to be limiting.

EXAMPLES

The present disclosure is further illustrated by the following examples, which should not be construed as limiting in any way.

Drug Delivery Module

Example 1A

Preparation of Alginate Microspheres

Dexamethasone loaded sodium alginate microspheres were prepared using a commercially available droplet generator (Nisco Engineering AG, Zurich). A solution of 2% w/v sodium alginate was filled into the syringe of 60 cc capacity. The flow rate of the solution was fixed according to the in-built program of the syringe pump. The encapsulation unit works on the principle of aerodynamic force where the sodium alginate solution while passing through the nozzle (diameter=0.35 µm) breaks up into micron size particles. The flow rate of sodium alginate solution was varied while the pressure was maintained at 70-75 mbar. The fine spray of alginate was collected into 250 mm calcium chloride solution for gelation under constant stirring (250 rpm) for 20 minutes. The microspheres obtained were separated by centrifugation and characterized for size by optical microscopy.

Example 1B

Optimization of Microsphere Size

Figure 2:
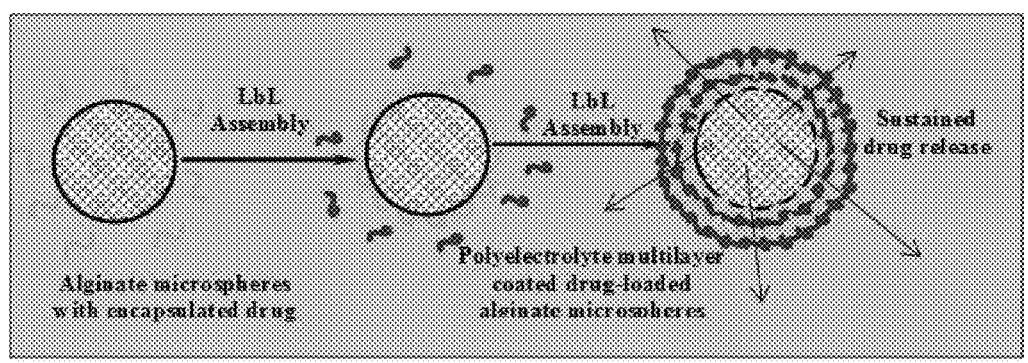
FIG. 2 is an image illustrating the mechanism of layer-by-layer assembly of microspheres.

To obtain uniform sized particles, different combinations of alginate concentration, flow rates, pressure and calcium chloride ($CaCl_2$) concentrations were used as shown in Table 1. Distance between the nozzle and vessel containing $CaCl_2$ solution also affects the size and morphology of the particles. Initially, 1.5% w/v alginate at a flow rate of 130 ml/h with 150 mbar pressures at 13 cm distance using 200 mm $CaCl_2$ concentration was used. Using these conditions, a mixture of particles (polydispersed) ranging from 40-120 µm were obtained. It was observed that particles of improved uniform size and regular spherical morphology were obtained when $CaCl_2$ concentration was changed from 200 mm to 250 mm. The average size of particles obtained after optimization was 60±5 µm as summarized in Table 1. Illustration of particle size distribution is charted in FIG. 1.

imide hydrochloride (EDC) as the cross linker and N-Hydroxysuccinimide (NHS) as a catalyst. The principle of the coupling chemistry involves the activation of carboxylic sites of alginate and reaction primary amine groups of PAA for a crosslinked coating towards increased retention of drug. Briefly, 10 ml of a 0.05 M phosphate buffered saline solution (pH 5.0) was prepared and 1 ml of $(PAH/PAA)_1$ coated alginate microspheres were transferred to the solution. To the same sample, 2.0 mg of EDC and 1.2 mg of NHS were dissolved and allowed to react while being stirred for 3 h. The spheres were then centrifuged to separate the unreacted EDC-NHS and rinsed three times before using them for the further studies. The surface charge of the microspheres was measured using the zeta potential analyzer after rinsing and prior to addition of each polyelectrolyte. The layer-by-layer coatings were analyzed using FTIR spectrometer wherein the microspheres were completely dried and mixed with potassium bromide before making measurement. Spectra were obtained on the spectrometer from 400 to 4000 $cm^{-1}$. The ζ-potential was calculated from the electrophoretic mobility using the Smoluchowski relation. 50 µl sample solution containing the polyelectrolyte coated microspheres was diluted in 2 ml of distilled water and used for analysis. Scanning electron microscope (SEM) images were also obtained to confirm the polyelectrolyte nanofilms deposition. Mechanism of layer-by-layer assembly of microspheres is illustrated in FIG. 2.

TABLE 1

Optimization of microspheres preparation

| S.No./Parameters | Alginate conc. (% w/v) | Flow rate (ml/h) | Pressure (mbar) | Cacl$_2$ conc. (mm) | Distance (cm) | Particle size (µm) |
|---|---|---|---|---|---|---|
| 1 | 1.5 | 130 | 150 | 200 | 13 | 40-120 ± 10 |
| 2 | 1.5 | 110 | 130 | 200 | 10 | 120 ± 10 |
| 3 | 1.5 | 90 | 110 | 200 | 9 | 100 ± 10 |
| 4 | 2.0 | 70 | 90 | 250 | 7 | 80 ± 10 |
| 5 | 2.0 | 30 | 55 | 250 | 2 | 60 ± 20 |
| 6 | 2.0 | 20 | 70 | 250 | 2 | 60 ± 5 |

Example 2A

Preparation of Polyelectrolyte Coating of Alginate Microspheres

Figure 3:
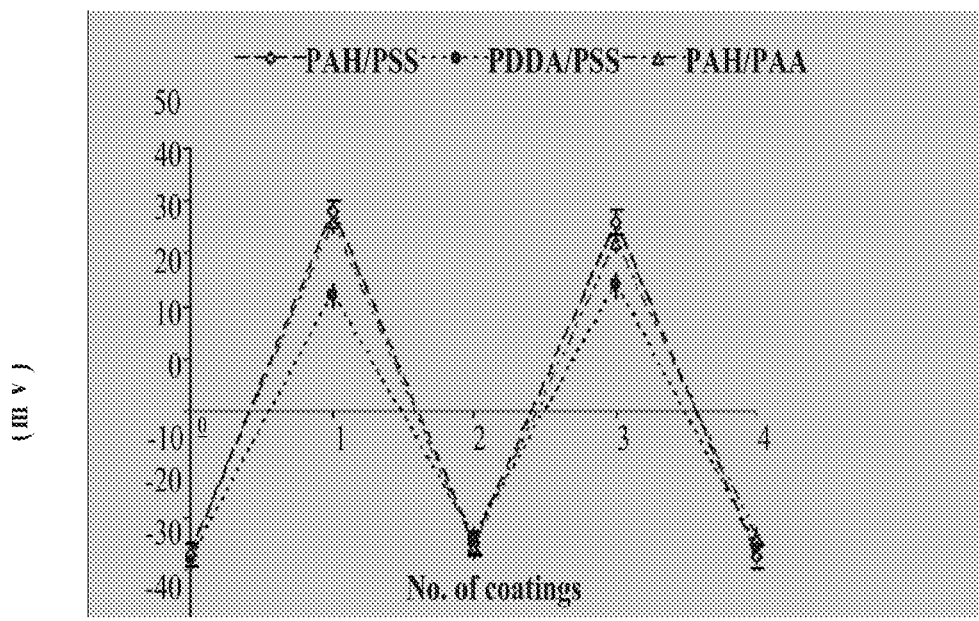
FIG. 3 is a graph illustrating zeta potential of uncoated and a variety of polyelectrolyte-coated alginate microspheres.

The polyelectrolytes used for this experiment were PSS, PAA, PAH and PDDA. A solution of 2 mg/ml concentration of each polyelectrolyte was prepared with 0.25 M $CaCl_2$ with pH adjusted to 7.4. For the coating, 3 ml of positively charged polyelectrolyte (PAH, PDDA) was added to 1 ml of calcium alginate microspheres and kept at room temperature for 20 min with intermittent shaking. The particles were then centrifuged at 500 rpm for 1 min to separate them from the unreacted polyelectrolyte solution and washed with distilled water. Later, 3 ml of negatively charged polyelectrolyte (PSS, PAA) was added to these microspheres and kept for 20 min intermittent shaking Finally, coated microspheres were washed twice with distilled water using centrifugation. The cross linking of PAH and PAA coated particles was performed using 1-Ethyl-3-[3-dimethyl aminopropyl]carbodi- Example 2B Results of Polyelectrolyte Coating of Alginate Microspheres Polyelectrolyte pairs including PAH/PSS, PDDA/PSS, PAH/PAA and crosslinked PAA/PAH were used to coat the drug loaded microspheres. To confirm successful deposition of nanofilms coatings on top of the alginate microspheres, zeta potential analysis was performed and the results are illustrated in FIG. 3, which clearly indicate reversal of surface charge with the deposition of each polyelectrolyte layer on microspheres. For charged microspheres, electrostatic interactions between the microspheres and the polyelectrolyte are the main driving force for multilayer build-up. These interactions have to be strong because otherwise the adsorbed layers would be removed upon adsorption of the next polyelectrolyte layer. The most significant peak in the infrared spectrum for alginate was at about 1600 $cm^{-1}$, contributed to carbonyl groups on alginate molecules. The peaks at 3400 $cm^{-1}$ and 3150 $cm^{-1}$ indicate the presence of —$NH_2$ groups, while the peaks at 1115 and 1170 cm$^{-1}$ indicate presence of —SO$_2^-$ groups. Cross linking of PAA/PAH coating was confirmed by FTIR studies. The peak at 3460 cm$^{-1}$ in case of cross linked microspheres indicate the presence of —NH$_2$ group, which confirm the chemical complexation of carboxylic acid groups on alginate with amine groups on NHSS.

Example 3A

Optimization of Drug Loading Concentration for In Vitro Drug Release

Varying concentrations of dexamethasone including 0.25, 0.50, 0.75 and 1.0 mg/ml were used to study the drug release from the uncoated alginate microspheres to achieve zero order release behavior. Each formulation was prepared in duplicate and each analysis was done in triplicate. Data was fitted to the model equations to ascertain the drug release mechanism.

Example 3B

Result of Effect of Drug Loading on In Vitro Drug Release

Figure 4:
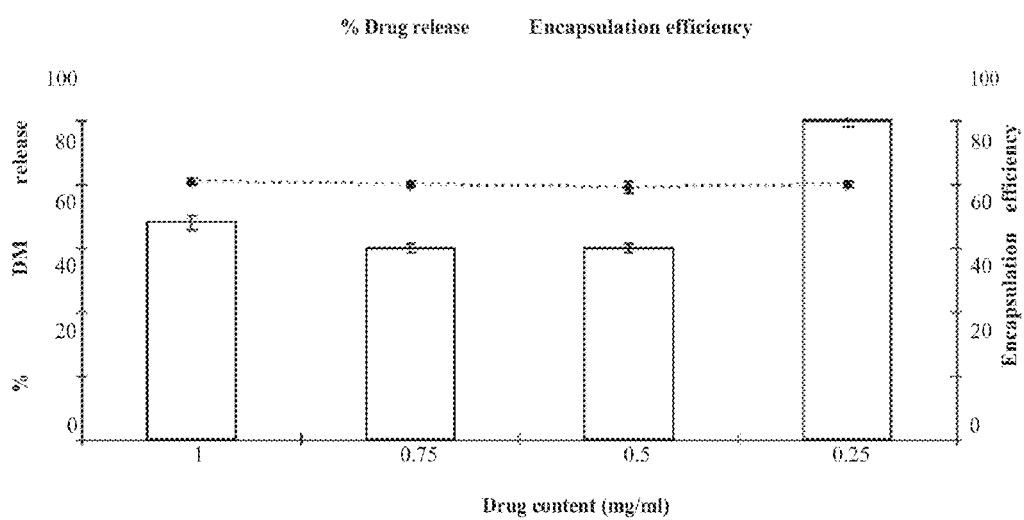
FIG. 4 is a bar graph illustrating the effect of drug loading on in vitro release behavior.

In order to achieve zero order release behavior for alginate microspheres, different concentrations of dexamethasone were used in the precursor alginate solution, including, e.g., 0.25, 0.5, 0.75 and 1 mg/ml. The % encapsulation efficiency and % drug release are both affected by changing the initial drug loading as shown in FIG. 4. As the drug content increases, there is influence on both types of release mechanism, i.e., the cumulative amount of drug released at any time (including burst release) and the drug release during induction period. Also, a higher amount of drug loading leads to an increase in the induction period causing drug release for a longer duration as in the case of 1 mg/ml approximately 80% in 30 days as compared to 100% release in case 0.25 mg/ml in 22 days. The desired system is expected to release 100% encapsulated drug within 4 weeks to in order to overcome the inflammatory response of the body to the implantable glucose sensor. Therefore, by decreasing the drug content from 1 mg/ml to 0.25 mg/ml, 100% drug release could be achieved with low burst release from uncoated alginate microspheres.

Example 4

Drug Release Methodology

Alginate microspheres were prepared as described above using dexamethasone sodium salt. The prepared microspheres were introduced in a dialysis membrane (molecular cutoff of 10-14 KDa) and transferred to a glass beaker containing 100 ml of phosphate buffered saline (PBS) (pH 7.4) and 0.01% w/v sodium azide (used to prevent the microbial contamination). The samples (in triplicate) were incubated in a 37±0.5° C. with constant agitation of 250 rpm for the release studies. 1 ml of buffer was periodically withdrawn from the beaker and replaced to maintain the drug concentration below 10% solubility. The amount of released dexamethasone in the collected medium was determined spectrophotometrically at λmax of 242 nm. All the in vitro release studies were conducted in triplicate (n=3), mean values and standard deviation were then calculated.

Example 5A

Polyelectrolyte Coating on Microspheres

Polycations including PAH and PDDA and polyanions including PSS and PAA were used for the study. Nanofilms coating were deposited according to the protocol described above. In vitro drug release studies were then completed according to the protocol described above. An additional coating involving chemically crosslinked PAH and PAA was also used as a part of this study. The chemical crosslinking was accomplished using a protocol described by Srivastava, R. et al., in *Macromol Biosci* 2005, 5, 717-727. Briefly EDC and NHSS were used in ratio of 1:0.6 and added to 1 ml of (PAH/PAA) coated microspheres under continuous stirring. The microspheres were then centrifuged to separate the unreacted EDC/NHSS and washed twice with distilled water before being used for the release study.

Example 5B

Results of Effect of Polyelectrolyte Coatings on In Vitro Drug Release Profile

Figure 5A:
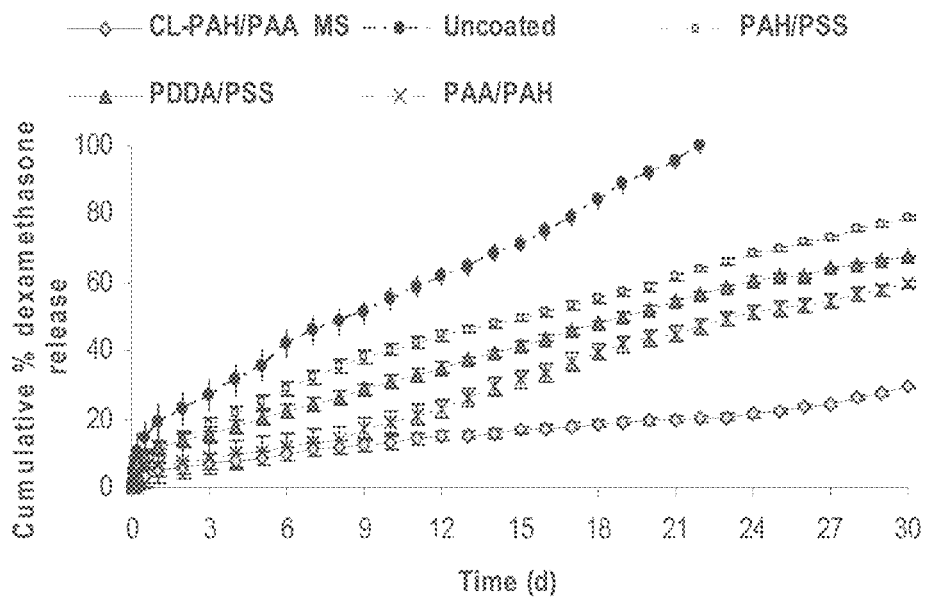
FIG. 5A is a graph illustrating the comparative release profile of uncoated and a variety of polyelectrolyte-coated dexamethasone loaded alginate microspheres in 0.01M PBS (pH 7.4) at 37° C. Mean±SD (n=3).
Figure 5B:
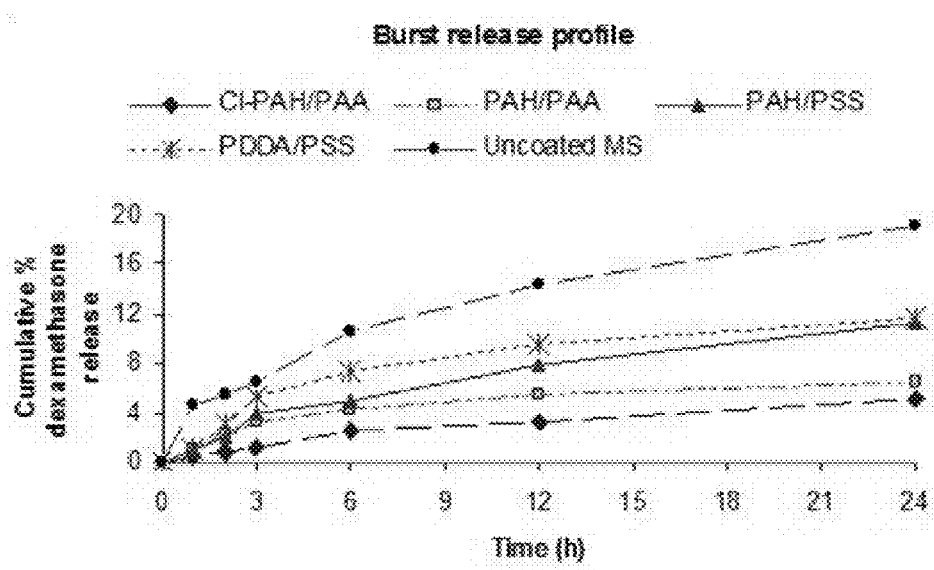
FIG. 5B is an illustration of the initial burst release profile of the microspheres over a period of 24 h.

The release behavior of the microspheres is mainly dependent on the polymer type, particle size, particle surface and specific interactions in the system. However, each parameter exhibits multiple effects on each part of the release profile and achieving a suitable release behavior involves identifying the main influences and manipulating the different parameters simultaneously to reach the desired release profile. Some parameters can be controlled so that the entire drug is released in the induction period to reduce release to a single continuous profile. The solution is to reduce the initial burst so as to maximize the amount of drug to be released in induction period. To achieve this objective, layer-by-layer self assembly technique was used to deposit nanofilm coatings on top of alginate microspheres, which is expected to result in better control over the release profile and a decrease in surface associated drug release. Polyelectrolyte layers act as a barrier to drug release and lead to a decrease in initial burst release due to an increase in diffusional path length that the drug has to traverse. The in-vitro release profile of uncoated and (PAH/PSS), (PDDA/PSS), (PAH/PAA) and EDC and NHSS cross linked (PAH/PAA) coated alginate microspheres are shown in FIG. 5A. The cumulative release from uncoated dexamethasone loaded microspheres was 100% in 22 days and 79%, 68%, 59% and 29% from coated microspheres in 30 days for (PAH/PSS), (PDDA/PSS), (PAH/PAA), and EDC and NHSS cross linked (PAH/PAA) microspheres, respectively. There was a significant difference (P<0.05) in the rate and extent of drug release as observed in uncoated and coated microspheres. Also, approximately 20%, 11%, 12%, 6.5% and 5% of the drug was released during initial burst phase from uncoated (PAH/PSS), (PDDA/PSS), (PAH/PAA) and cross linked (PAH/PAA) coated alginate microspheres in the first day, respectively (shown in FIG. 5B).

A biphasic pattern was observed which is characteristic of matrix diffusion kinetics. Data was fitted to Zero order kinetics model equation. However, 100% drug release was not obtained in the case of polyelectrolyte coated microspheres over a period of 30 days. Therefore, to achieve 100% drug release, a various ratiometric combination of uncoated and (PAH/PSS)$_1$ coated microspheres was used.

Example 6A

Effect of Different Ratios of Uncoated and (PAH/PSS) Coated Microspheres on Dexamethasone Release To achieve a zero order release profile, various combinations of uncoated and (PAH/PSS) coated dexamethasone loaded microspheres were taken in different ratios, e.g., 25% coated to 75% uncoated, 50% coated to 50% uncoated and 75% coated to 25% uncoated and further used for in vitro release studies.

Example 6B

Figure 6A:
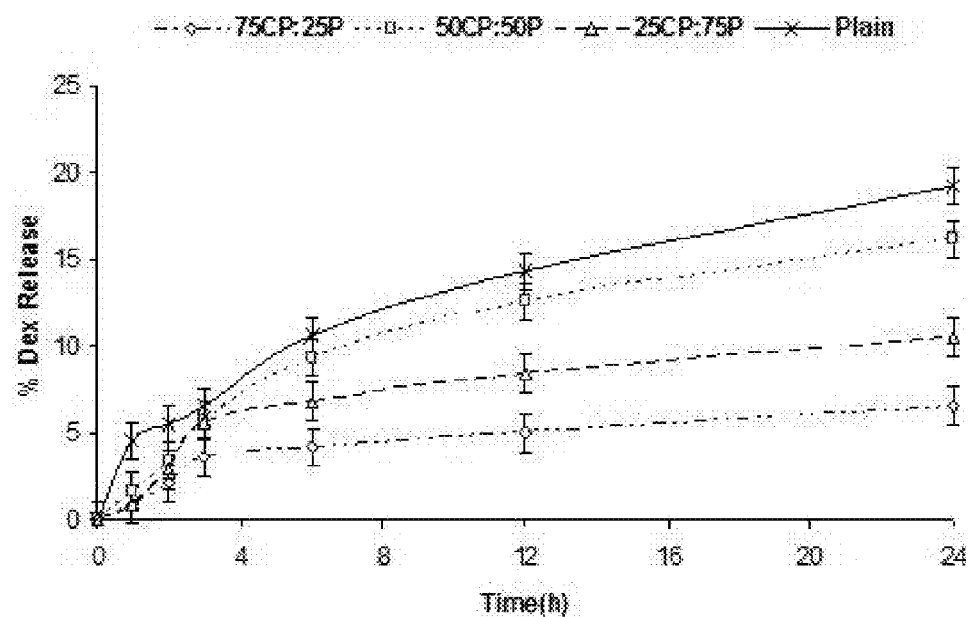
FIG. 6A is an illustration of the initial burst release profile of the microspheres over a period of 24 h.
Figure 6B:
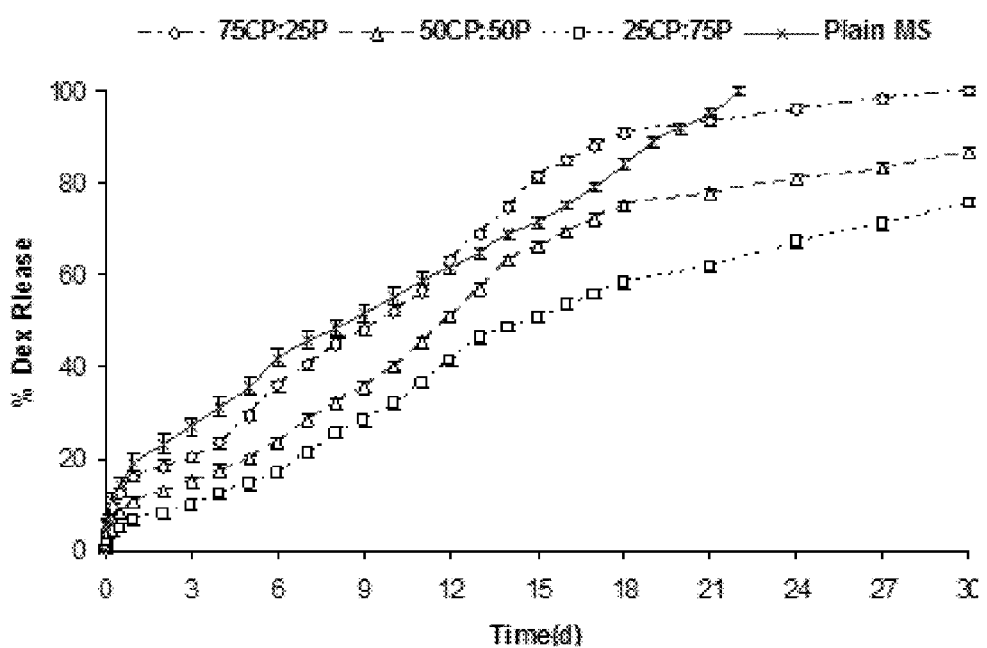
FIG. 6B is a graph illustrating the comparative release profile of different ratios of uncoated and different polyelectrolyte coated dexamethasone loaded alginate microspheres in 0.01M PBS (pH 7.4) at 37° C. Mean±SD (n=3).
Figure 6C:
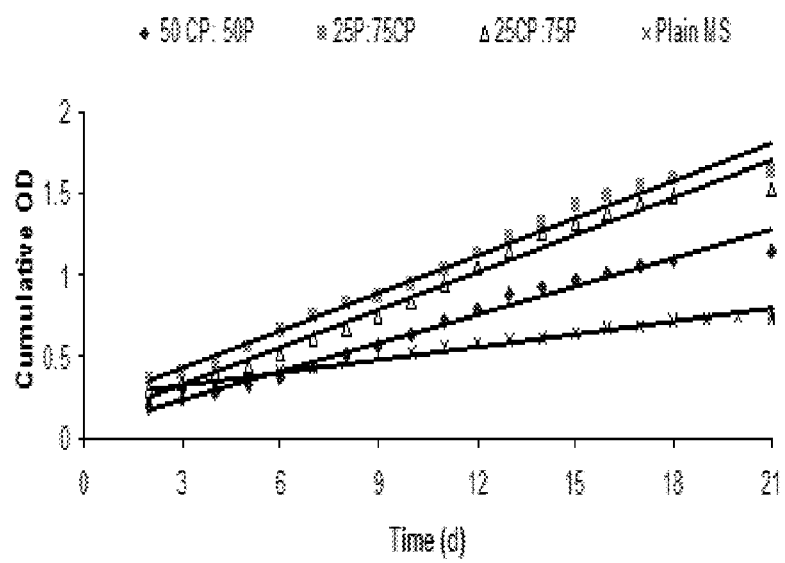
FIG. 6C illustrates the zero order release kinetic data for the microspheres.

Results of Different Ratios of Uncoated and (PAH/PSS) Coated Microspheres on Dexamethasone Release Different combinations of uncoated and (PAH/PASS) coated microspheres, e.g., 25CP:75P, 50CP:50P and 75CP:25P (CP-Coated particles and P-Plain particles) were used to achieve zero order release behavior. For the plain microspheres, initial burst release was 19.25% and for 25CP:75P, 50CP:50P and 75CP:25P, it was 10.50%, 16.11% and 6.54% respectively as shown in FIG. 6A. The release profile showed zero order release kinetics after a burst release period, which lasted for 1 day. The cumulative release of uncoated and different combinations of uncoated and (PAH/PASS) coated dexamethasone loaded microspheres including 25P:75CP, 50P:50CP and 75P:25CP was 100%, 98.94%, 86.63% and 75.71%, respectively, as shown in FIG. 6B. There was a significant ($P<0.05$) difference in the rate and extent of drug release as observed in uncoated and different combinations of uncoated and (PAH/PASS) coated microspheres. The 25P:75CP combination showed only 6.54% burst release as compared to 19.25% in the case of uncoated microspheres with 100% dexamethasone release in 30 days as compared to 22 days with uncoated microspheres. Thus, 100% dexamethasone was released with zero order kinetics for a period of 30 days as shown in FIG. 6C.

Figure 7:
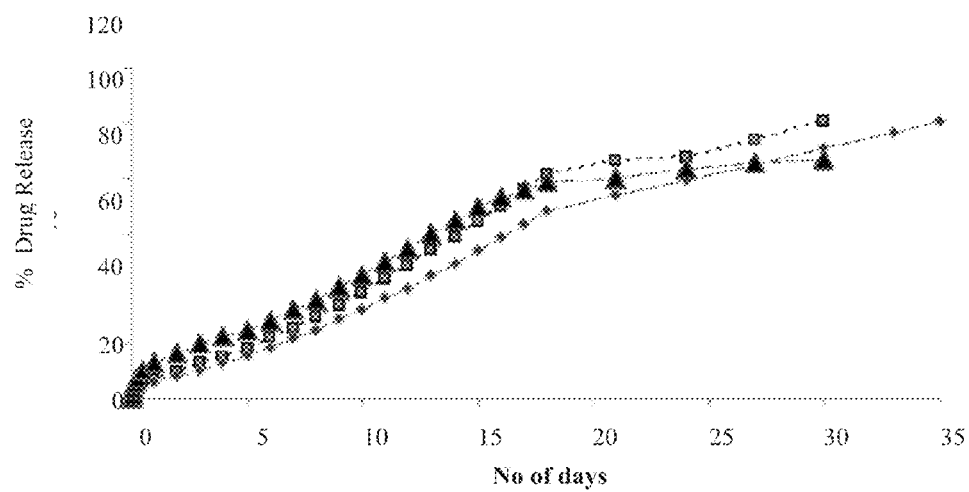
FIG. 7 is an image illustrating comparative release profile of uncoated diclofenac loaded alginate microspheres in PBS (pH 7.4) containing sodium azide (0.1%) at 37° C., Mean±SD (n=3).

System acceptability was also checked by Diclofenac as a model drug. Drug release over a period of 30-35 days was controlled. FIG. 7 shows the result of diclofenac release from alginate microspheres. Drug release can be modulated by changing the drug loading concentration or by increasing the number of polyelectrolyte bilayers on top of the drug loaded microspheres.

Animal Studies

Example 7

In Vivo Experiments to Assess Pharmacodynamic Changes

Drug loaded microspheres were prepared and suspended in a viscosity enhanced diluent (30 mg/ml carboxymethylcellulose sodium salt, 9 mg/ml NaCl and sterile water) in order to prevent any sticking of the microspheres in syringes/needles during injection. Rats were anesthetized in an induction chamber filled with a 4.5% (v/v) mixture of isofluorane in oxygen. The back of each animal, where microspheres were injected, was shaved prior to injection. 100 μl of alginate microspheres dispersed in vehicle were injected subcutaneously using 20 gauge needles. Microspheres were administered at 1 mg dexamethasone encapsulated dose per animal. Rats were sacrificed at each of the following time intervals: 7, 14, 21, and 30 days for control, drug loaded and plain microspheres.

Example 8

Pharmacodynamics: Histopathological Evaluation

Standard histological protocols were used. Hematoxylin and eosin (H&E) staining method was used to characterize and quantify the inflammation-mediating cells in the vicinity of the microsphere in response to the inflammation induced by implantation and by the continued presence of the implants. To cover the maximum possible area surrounding the implant, blood vessels and inflammation mediating cells were counted randomly and chosen regions of equal area in each photomicrograph was taken. For inflammation cell counts, the final values reported are an average from five regions counted in photomicrographs from five different rats per time point±standard deviation. For blood vessel counts, the final values are reported as counted in photomicrographs. Tissue samples from the rat studies described above were fixed in 10% formalin and sections were immersed in paraffin and cut using a microtome. Plain microspheres were used as a positive control and untreated subcutaneous tissue samples were used as a negative control. Photomicrographs of the histology slides were taken and digitally stored using an Olympus microscope at 10-100× magnification. Visual counting of the purple stained nuclei of the inflammatory cells is performed to reduce error.

Example 9

Pharmacodynamics of Inflammation Control

Figure 8:
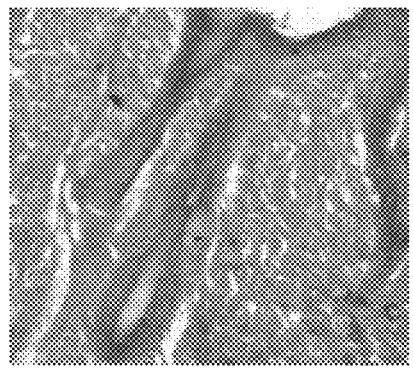
FIGS. 8A-8E are images illustrating pharmacodynamic changes of various microspheres injected subcutaneously in representative Sprague Dawley rats after 7, 14, 21, and 30 days. The rats were sacrificed and the implant site was dissected, processed and stained using hematoxylin and eosin (H&E). Inflammation is evident in the positive control (plain microspheres), while normal tissue can be seen in untreated tissue section (negative control-top panel).
Figure 8:
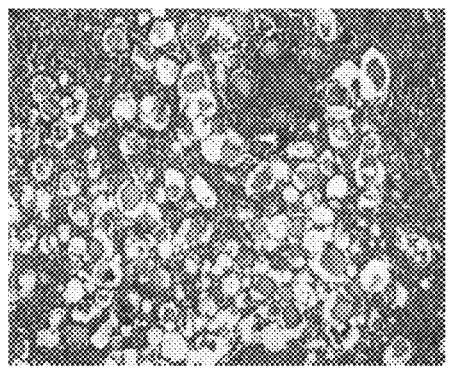
Figure 8:
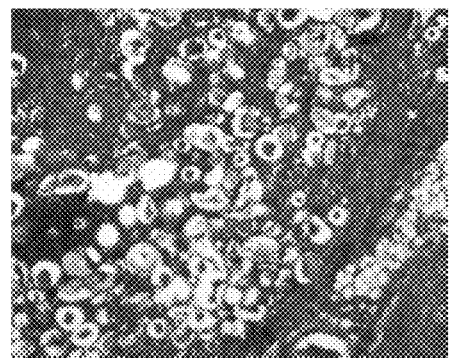
Figure 8:
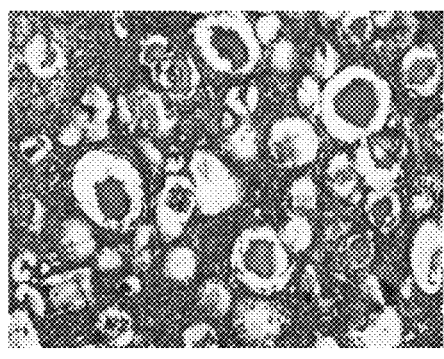
Figure 8:
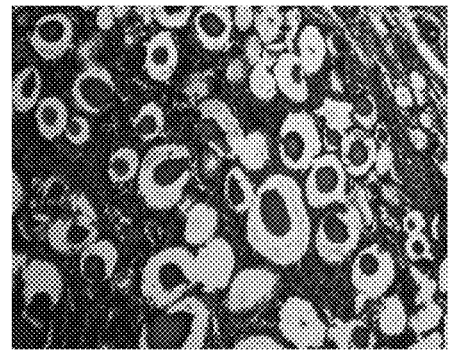

Localized delivery of corticosteroids or anti inflammatory agents can reduce the immunostimulatory cascade of events and facilitate wound healing. To investigate the effect of the dexamethasone on the local tissue environment, the following controls were also studied: 1) drug-free microspheres (MS); 2) combination of coated (CP) and uncoated (P) MS in the ratio of 25P:75CP; 3) Apo-GOx alginate sensor; and 4) combination of Apo-GOx alginate sensor with dexamethasone loaded MS in 50:50 ratio. Tissue samples surrounding the composites containing no drug demonstrate typical negative reactions associated with trauma inflicted during the implantation procedure as well as those observed due to the continuous presence of the implant in the subcutaneous space as shown in FIG. 8.

Implantation-associated trauma stimulates humoral and cellular immunogenic response that is characterized by immediate infiltration of inflammation-mediating cells, specifically neutrophils. The neutrophils are followed by macrophages, polymorphonuclear leukocytes, monocytes, fibroblasts and eventually, giant cells form. The inflammation mediating cells surrounding the implant site during the acute phase of inflammation are stained purple using H&E, whereas normal tissue is stained pink. Prolonged in vivo residence of the implant causes the acute inflammatory reaction to advance to the chronic phase, which is characterized by the deposition of fibrotic tissue around the implant and a decrease in the number of inflammation-mediating cells. By week four, there was an aggressive formation of a dense fibrotic capsule that completely entombed the implant, as is observed in FIG. 8.

Similar immunological reactions have been previously shown to occur in the presence of drug delivery systems as well as polymeric materials such as polyester, polyethylene, oligo(poly(ethylene glycol) fumarate), poly(caprolactone), on poly(ethylene oxide), poly(dimethyl siloxane), and polyurethane used in the manufacture of implants, stents, and prosthetic and other bio-medical drug delivery devices. This humoral and cellular response characterized by massive infiltration and subsequent apoptosis of the immune cells may change the immediate tissue composition surrounding the implant with plain skin as negative control. Inflammation-mediating cells and normal cells are stained purple and pink, respectively (H&E staining).

Figure 9:
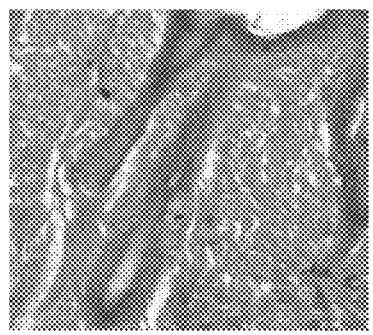
FIGS. 9A-9E are images illustrating pharmacodynamic changes in representative subcutaneous tissue sections of rats implanted with 25P:75CP DEX loaded microspheres over 4 week post-implantation with plain skin as negative control. Inflammation-mediating cells and normal cells are stained purple and pink, respectively (H&E staining).
Figure 9:
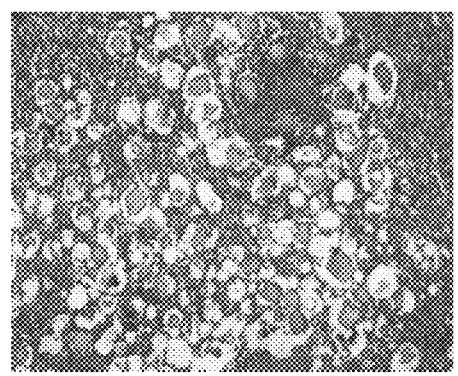
Figure 9:
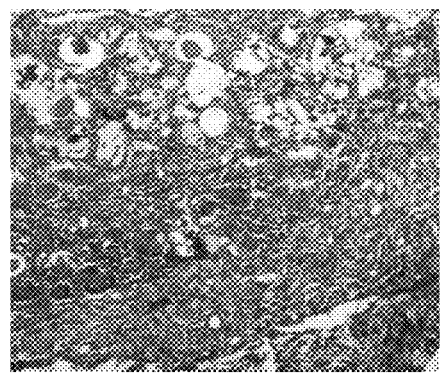
Figure 9:
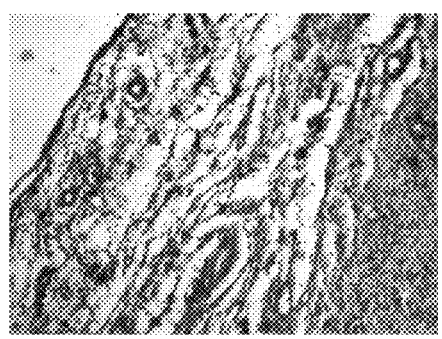
Figure 9:
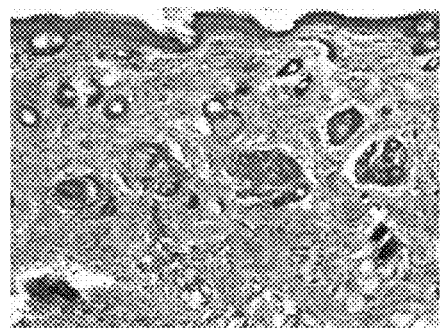
Figure 10:
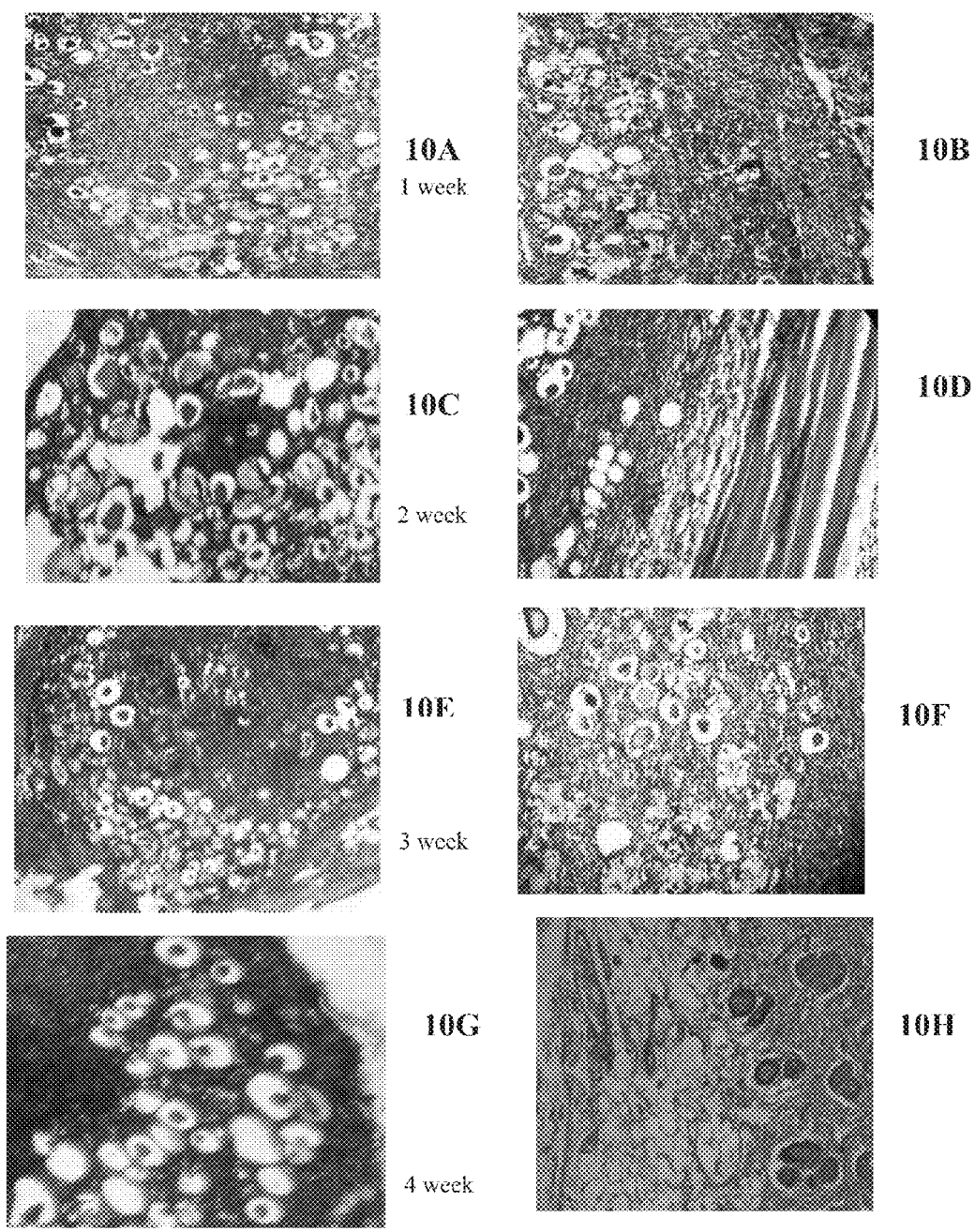
FIGS. 10A-10H are images illustrating pharmacodynamic changes in representative subcutaneous tissue sections of rats implanted with (I) Apo-GOx alginate sensor (10A-10D), (II) Apo-GOx sensor+(25P:75CP) dexamethasone loaded alginate MS (10E-10H) over week 1, week 2, week 3, and week 4 post-implantation. Inflammation-mediating cells and normal cells are stained purple and pink, respectively (H&E staining).

Since the cellular composition of fibrotic tissue is different from that of normal (untraumatized) tissue, drug release from entombed implanted sustained release delivery systems can be potentially altered and the desired pharmacological effects may not be achieved. The presence of fibrous capsules is particularly detrimental for biosensor applications since such capsules can be impervious to the transfer of the small molecular weight analytes of interest to the sensor surface. Thus, it is critical to maintain a well-vascularized fibrosis-free environment to ensure successful performance of implantable bio-medical devices. FIG. 9 and FIG. 10 depict the pharmacodynamic changes at the implant site when dexamethasone was incorporated with Apo-GOx sensor or alone as compared to positive control. The infiltration of precursor molecules such as prostaglandins and leukotrienes is responsible for inflammation mediation. As clearly observed, the subcutaneous tissue surrounding the Apo-GOx sensor implant looks similar to natural tissue. In addition, to slow the acute inflammatory phase, the dexamethasone releasing implants prevented progression to the chronic inflammatory phase as evident by the lack of fibrotic tissue surrounding the implant on weeks 3 and 4. Suppression of the generalized immune response is attributed to the inhibition of cellular pathways involved in the biosynthesis of inflammation-mediating cells in the vicinity. This lack of fibrous deposition but enhanced inflammation is speculated to be due to the complex cellular functions. Localized elution of dexamethasone led to a statistically significant decrease in the number of inflammation cells surrounding the implant during the acute as well as chronic phases of inflammation. Inflammation was significantly reduced in the tissue surrounding the dexamethasone microspheres compared to the positive control (empty microspheres) and the number of inflammatory cells was approximately similar to that of normal tissue.

Glucose Biosensing Module

Example 10

Preparation of Calcium Alginate Microspheres

Alginate microspheres were prepared by the emulsification technique reported by Srivastava et al., *Macromol Biosci* 2005, 5, (8), 717-27; Srivastava et al., *Biotechnol Bioeng* 2005, 91, (1), 124-31; and Srivastava et al., *J Microencapsul* 2005, 22, (4), 397-411. The oil phase consisted of a mixture of 0.0424 gm of SPAN 85 and 1.85 gm isooctane. 1.25 gm of 3 wt % sodium alginate aqueous solution was added slowly drop wise to the oil phase while being continuously stirred. The solution was allowed to stir for an additional 15 min at 500 rpm. A solution containing 0.0226 gm of TWEEN 85 in 0.125 gm of isooctane was then added to the emulsion and stirred for another 15 min at 500 rpm to achieve stable water/oil emulsion droplets. After this, 500 µl of aqueous solution containing 5 wt % of calcium chloride was added to induce formation of ionic crosslinks, and was allowed to stir for about 1 h. The microspheres were then diluted to prevent aggregation and further rinsed with DI water by successive centrifugation cycles and stored in DI water at room temperature. Thereafter, microspheres were characterized using scanning electron microscopy (SEM).

Example 11

Preparation of Apoenzyme (Apo-Glucose Oxidase)

Apo-glucose oxidase preparation involves removal of flavin adenine dinucleotide (FAD) from the holoenzyme glucose oxidase. The apoenzyme was prepared using the Swoboda protocol (Swoboda, B. E., *Biochem Biophys Acta* 1969, 175, (2), 365-79) with some modifications. Glucose oxidase (20 mg) was dissolved in 1 ml of 0.4 M sodium acetate buffer (pH=5), and this solution was slowly added drop wise to 20 ml of 25% saturated ammonium sulfate (pH=1.4). The sample was then incubated in an ice bath with constant stirring for 2 h. After this, 100% saturated ammonium sulfate solution was added to the above solution to separate out the flavin adenine dinucleotide (FAD) from the glucose oxidase protein. The solution was then centrifuged twice at 16,000 rpm for 15 minutes at 0° C. The yellow supernatant (FAD) was then removed, and precipitate dissolved and neutralized by adding 2.5 M sodium acetate buffer. The precipitated protein was finally redissolved in 0.1 M sodium acetate buffer (pH=5.6). The protein was eluted through NAPS columns to concentrate the protein and separate out the dissolved ammonium sulfate salt from the protein. Sodium bicarbonate buffer was used for elution so as to allow dye labeling of apoenzyme. A UV-Vis spectrophotometer was used to confirm the removal of FAD and to calculate to concentration of the apoenzyme.

Example 12

Preparation of Labeled Sensing Reagents

Concavalin-A (Con A) was conjugated with TRITC dye using a standard amine labeling procedure (Svensson, H. P. et al., *Bioconjugate Chemistry*, 1992, 3, (2), 176-81). Briefly, a solution containing 20 mg/ml TRITC dissolved in DMSO was added to the Con A solution under constant stirring. The reaction mixture was then incubated in the dark for 4 h at room temperature under continuous stirring. Finally, the mixture was eluted through PD-10 desalting columns to separate out the TRITC-labeled Con A from the unconjugated dye. The concentration of the labeled Con A was calculated to be 10 µM with degree of labeling of 1.

Apo-GOx was also conjugated with TRITC dye using a standard amine labeling procedure as described in Svensson et al. Briefly, a solution containing 20 mg/ml TRITC dissolved in DMSO was added to the obtained apoenzyme solution under constant stirring. The reaction mixture was then incubated in the dark for 4 h at room temperature under continuous stirring. Finally, the mixture was eluted through PD-10 desalting columns to separate out the TRITC-labeled apo-GOx from the unconjugated dye. The concentration of the labeled apo-GOx was calculated to be 10 µM with degree of labeling of 1.

For the NIR sensor system, dextran amino was labeled with Alexa Fluor-647 donor dye while apo-glucose oxidase was labeled with QSY-21 quencher acceptor dye. The reaction mixture was incubated in the dark for 1 h at room temperature under continuous stirring. The concentration of the labeled apoenzyme was calculated to be 1.3 µM with degree of labeling of 2, while the concentration of labeled dextran amino was calculated to be 2 μM with degree of labeling of 2.

Example 13

Fabrication of Multilayered Thin Film Coated Alginate Microsphere Sensors

Alginate microspheres loaded with the sensing assay were prepared using the technique described in the earlier section with the following modifications. A 1 μm solution of fluorescein isothiocyanate (FITC)-dextran (FD) was mixed with 10 μM tetramethylrhodamine isothio-cyanate (TRITC)-Con A/TRITC-apo-GOx solution and used for co-encapsulation. The sensing reagents were then mixed in 2% w/v sodium alginate solution in a ratio of 1:10 by volume. The solution was gently agitated for about 30 min in the dark to prevent photobleaching of the dye while allowing complete mixing in the precursor solution. Calcium alginate microspheres were then prepared using the emulsification technique. Thereafter, multilayered thin film polyelectrolyte coatings (2 bilayers) were deposited over the alginate microspheres containing the fluorescent sensing assay using the layer by layer self assembly technique as described previously.

Similarly, for the near-infrared system, AF-647-dextran amino (2 μM) and QSY-21-apo-glucose oxidase (1.3 μM) were mixed together in 4:1 volume ratio under stirring for 30 min in the dark. The sensing reagents were then mixed in 2% w/v sodium alginate solution in a ratio of 1:10 by volume. The solution was gently agitated for about 30 minutes in the dark to prevent photobleaching of the dye while allowing complete mixing in the precursor solution. Calcium alginate microspheres were then prepared using the emulsification technique. Thereafter, multilayered thin film polyelectrolyte coatings (2 bilayers) were deposited over the alginate microspheres containing the fluorescent sensing assay using the layer by layer self assembly technique as described previously.

Example 15

Layer by Layer Self Assembly Technique

For the Layer-by-Layer (LbL) coatings on top of alginate microspheres loaded with sensing chemistry, solutions of PAH (cationic) and PSS (anionic) used for assembling [PAH/PSS] multi-layers, were prepared in DI water at 2 mg/ml with 250 mm calcium chloride salt. As the core particles are negatively charged, they were dispersed in 2 ml of 2 mg/ml PAH solution for 20 min, followed by two consecutive washing steps to remove excess polyelectrolyte and 2 mg/ml of PSS solution for 20 min to complete one bilayer.

Example 16

Partial Dissolution of Alginate Microsphere Core

The mesh size of the hydrogel can be increased through introduction of an aqueous solution to the precursor solution, reducing the potential for cross-linking But this addition of aqueous solution does result in increased leaching of the sensing assay components encapsulated inside the hydrogel, thereby reducing the time span of a sensor.

The diffusion through a hydrogel decreases as the cross-linking increases. The sensing assays and the target analytes diffuse more quickly through dissolved-core alginate microspheres as compared to non-dissolved alginate microspheres. The time response of non-dissolved alginate microspheres is much slower as compared to the dissolved-core alginate microspheres. This may be attributed to the lack of free space required during competitive binding inside the hydrogel network within the alginate microsphere. It can be hypothesized that, on addition of glucose, the spatial displacement of molecules within the hydrogel network was slow and limited, resulting in minimal changes in fluorescent intensities. Therefore, the dissolved-core alginate microspheres were designed to increase the sensitivity and time response of the final sensor.

In the present study, sodium citrate was used for removal of the $Ca^{2+}$ ions. As the $Ca^{2+}$ ions are removed, the crosslinking in the gel decreases and this leads to solubilization of the high molecular weight alginate polymers. The polyelectrolyte coatings do not dissolve in the presence of $Ca^{2+}$ chelators and thus stabilize the alginate microspheres while simultaneously preventing the leakage of the sensing chemistry. To dissolve the core, 0.1M sodium citrate-TRIS HCl solution was added to a suspension of alginate microspheres and kept for 2-3 days. The suspension was then centrifuged and washed twice to remove excess solution.

Non-dissolved particles exhibited insignificant changes in fluorescence intensity on addition of glucose, and the time to reach steady state is much slower (approximately 6-7 min). The alginate is permeable to glucose, and the slow response time is attributed more to the physical restriction of the large dextran molecules resulting in an extremely slow spatial displacement of molecules within the hydrogel network and minimal changes in fluorescent intensities. Therefore, non-dissolved alginate microspheres were disregarded because of the limited mobility it offered to the encapsulated sensing assay.

Degradation of $Ca^{2+}$ crosslinked alginate gel can be accomplished by the use of a chelating agent such as ethylene glycol-bis(β-aminoethyl ether)-N,N,N',N'-tetracetic acid (EGTA), ethylenediaminetetraacetic acid disodium salt dihydrate (EDTA), lactate, citrate, and phosphate, or by a high concentration of ions such as $Na^+$ or $Mg^{+2}$.

Example 17

Characterization of Core Dissolution

The partially dissolved core of alginate microspheres was characterized using SEM, EDX and confocal laser scanning microscopy (CLSM) analysis. For CLSM analysis, calcium alginate microspheres were prepared by directly labeling the alginate with FITC, using a technique reported earlier. The prepared FITC labeled alginate was then mixed with sodium alginate solution to fabricate labeled calcium alginate microspheres. The dissolution of core was studied by subjecting the alginate microspheres to different levels of citrate treatment for three days. The CLSM images and line scan data of microspheres treated with citrate depicted a folded appearance and uneven distribution of FITC-alginate, which clearly indicates a change in the structure and dye distribution.

Example 18

Sensing Assay and Dye Ranges

Description of precise assembly of the visible sensing assay (FITC-dextran-TRITC-Con A/FITC-dextran-TRITC-apo-GOx) and near infrared sensing assay (AF-647-dextran amino-QSY-21-apo-GOx) co-encapsulated inside polymeric hydrogels to dissolved-core alginate templated microspheres is described. Feasibility and functionality of competitive binding assays within polyelectrolyte-coated dissolved-core alginate microspheres for glucose sensing was assessed. The response of two different systems (FITC-dextran-TRITC-apo-GOX/AF-647-dextran-amino-QSY-21-apo-GOx) encapsulated within dissolved core alginate microspheres was compared.

Example 19

Dye Ranges

| Visible dye ranges | | | |
|---|---|---|---|
| Donor | FITC | excitation 488 nm | emission 520 nm |
| Acceptor | TRITC | excitation 555 nm | emission 580 nm |

| NIR dye ranges | | | |
|---|---|---|---|
| Donor | AF-647 | excitation 647 nm | emission 665 nm |
| Acceptor | QSY21 | absorption max = 661 nm | |

The incorporation of long wavelength NIR dyes enables more efficient excitation through scattering tissue, which effectively improves the odds of successful use in vivo. The skin exhibits substantial interfering fluorescence at shorter wavelengths. The near-infrared dyes offer a better potential than fluorescent dyes because they have higher detectability due to high absorbance ($>10^5$ $M^{-1}$ $cm^{-1}$ at long wave peak) and higher quantum yield. The near-infrared region falls in the range 600 nm to 1300 nm, which is the so called optical window in human body tissues. The $v^4$ dependence of intensity of scattered light means that many samples that appear murky in visible light, such as macroscopic tissue samples, are substantially transparent to infrared light, thus avoiding the problem of any background fluorescence and noise during the optical monitoring of the implanted biosensors from outside the body. In addition to the above, the NIR light also passes through several centimeters of tissue.

Dyes that quench the fluorescence of excited fluorophores are increasingly important for use in proximity studies like FRET. The quencher dyes act as efficient energy transfer acceptors in FRET applications. QSY-21 quencher dye has a broad and intense absorption maximum (661 nm), but no fluorescence, making it useful as an acceptor in FRET applications. It has a quenching range of 590 nm-720 nm. The non-fluorescent acceptors offer the advantage of eliminating the potential problem of background fluorescence resulting from direct acceptor excitation (non-sensitized). Thus, there is lower background fluorescence and the transferred energy is dissipated as heat.

Figure 11:
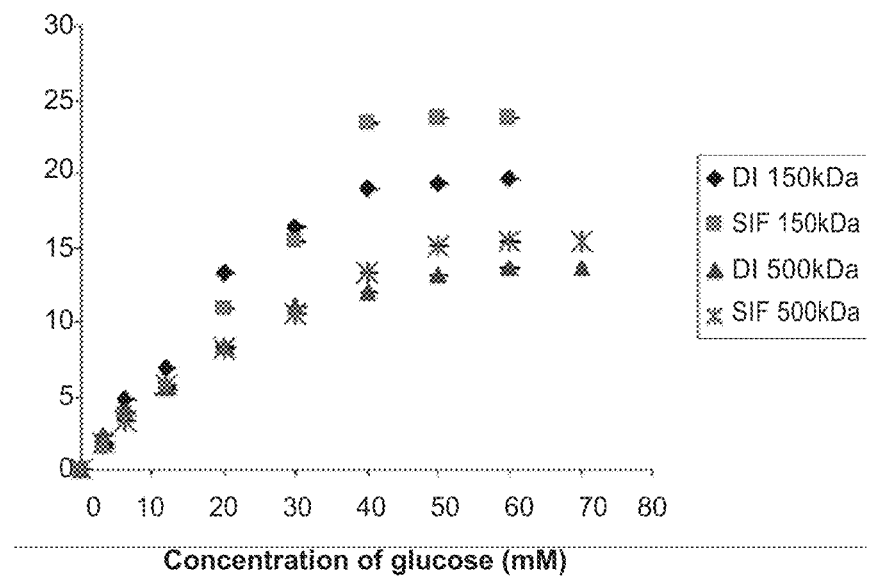
FIG. 11 is a graph illustrating glucose sensitivity curve for alginate microsphere (FD (150/500 kDa)-TRITC-ConA) suspension in water and simulated interstitial fluid. Mean±SD (n=5).

It can be observed from FIG. 11, the glucose sensitivity of the encapsulated TRITC-Con A/FITC-dextran (500 kDa) assay in DI water was estimated to be 0.26%/mm glucose, while that in simulated interstitial fluid was observed to be 0.3%/mm glucose; and both demonstrated a linear response in the range of 0-50 mm glucose. Whereas, the glucose sensitivity of the encapsulated TRITC-Con A/FITC-dextran (150 kDa) assay in DI water was estimated to be 0.47%/mm glucose, while that in simulated interstitial fluid was observed to be 0.59%/mm glucose; and both demonstrated a linear response in the range of 0-40 mm glucose.

Figure 12:
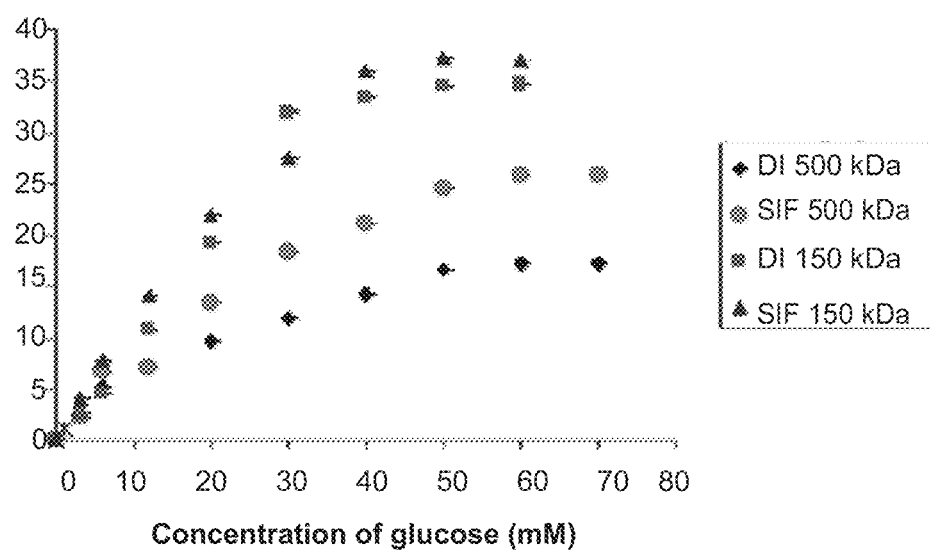
FIG. 12 is a graph illustrating glucose sensitivity curve for alginate microsphere (FD (150/500 kDa)-TRITC-apo-GOx) suspension in water and simulated interstitial fluid. Mean±SD (n=5).

It can be observed from FIG. 12 that the glucose sensitivity of the encapsulated TRITC-apo-GOx/FITC-dextran (500 kDa) assay in DI water was estimated to be 0.33%/mm glucose, while that in simulated interstitial fluid was observed to be 0.5%/mm glucose; and both demonstrated a linear response in the range of 0-50 mm glucose. The glucose sensitivity of the encapsulated TRITC-apo-GOx/FITC-dextran (150 kDa) assay in DI water was estimated to be 0.84%/mm glucose, while that in simulated interstitial fluid was observed to be 0.9%/mm glucose; and both demonstrated a linear response in the range of 0-40 mm glucose.

A difference was observed in the glucose sensitivity for different molecular weight FD molecules for the encapsulated FD/TRITC-Con A/apo-GOx system. The 500 kDa FD system again exhibited a wider range of response, but lower sensitivity, than the 150 kDa FD system. The glucose sensing results have been summarized in Table 2.

TABLE 2

Summary of Glucose Sensing Results

| Sensor system (Alginate microsphere biosensor) | Response range (mm) | | Glucose sensitivity (% change/mm glucose) | |
|---|---|---|---|---|
| | DI water | SIF | DI water | SIF |
| FD-150kDa/TRITC-ConA | 0-40 | 0-40 | 0.47 | 0.59 |
| FD-500kDa/TRITC-ConA | 0-50 | 0-50 | 0.26 | 0.3 |
| FD-150kDa/TRITC-apo-GOx | 0-40 | 0-40 | 0.84 | 0.9 |
| FD-500kDa/TRITC-apo-GOx | 0-50 | 0-50 | 0.33 | 0.5 |

Example 20

NIR Dye System

Figure 13:
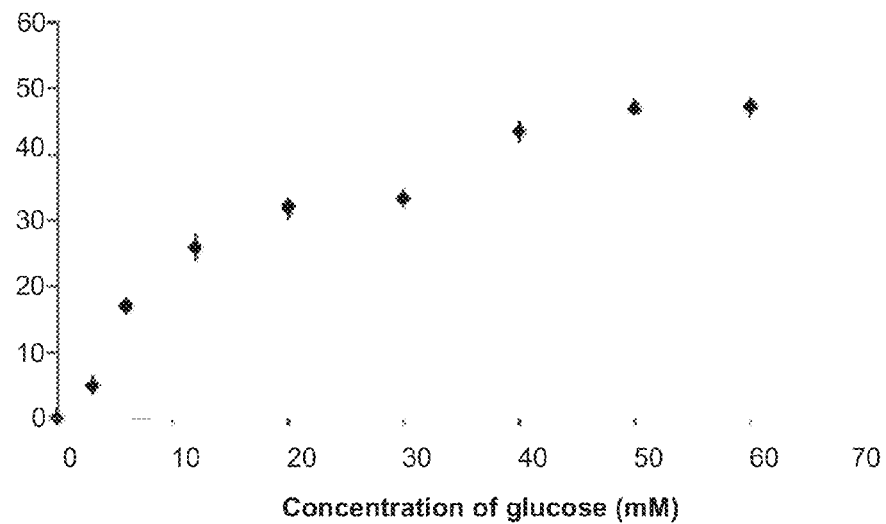
FIG. 13 is a graph illustrating glucose sensitivity curve for alginate microsphere sensors loaded with AF-647-dextran amino (500 kDa)-QSY-21-apo-GOx. Mean±SD (n=5).

Initially, a fluorescent emission scan was collected for the dissolved core alginate microspheres suspension loaded with AF-647-dextran amino and QSY-21-apo-glucose oxidase by exciting sample at 620 nm. Fluorescence spectra were then collected after titration of increasing concentrations of 3 mm to 60 mm β-D glucose solution into the alginate microspheres. Sensitivity curves were obtained by plotting the percentage change in AF peak intensity versus glucose concentration. On plotting the glucose sensitivity curve, an increase in AF-647 fluorescence was observed up to 50 mm glucose as illustrated in FIG. 13. The corresponding glucose sensitivity was calculated to be 0.94%/mm glucose.

Example 21

In Vitro Cytotoxicity Studies

The cytotoxicity of the uncoated alginate microspheres and (PAH/PSS)$_2$ coated alginate microspheres with the fluorescent glucose sensing assay were evaluated by using sulforhodamine-B (SR-B) semi-automated assay. An in vitro biocompatibility study of these samples was performed using L929 (Mouse fibroblasts) cell lines obtained from the National Centre for Cell Science (NCCS), Pune, India. The cells were grown in modified DMEM (Dulbecco's modified essential medium, Sigma, USA) supplemented with 10% FBS (fetal bovine serum, Sigma, USA) and 1% antibiotic/antimycotic solutions (Himedia, India) and incubated at 37° C. temperature under 5% $CO_2$ and saturated humid environment. Nearly confluent cells in 25 $cm^2$ tissue culture flasks were trypsinized by trypsin-EDTA (ethylene diamine tetra acetic acid) solution and centrifuged at 1000 g for 10 min. The cell pellet was then resuspended in fresh media. Cells were counted and cell count was adjusted accordingly to the titration readings so as to give an optical density in the linear range (from 0.5 to 1.8). Samples were tested in 96 well plates in 3 triplicates, each well receiving 90 µl of cell suspension with a concentration of $1 \times 10^4$ cells per well. The plate was then incubated at 37° C. in $CO_2$ incubator for 24 h. 10 µL of diluted polyelectrolyte coated and uncoated alginate microspheres were added after 24 h incubation to the 96 well-plate and further incubated for 48 h. Finally, the experiment was terminated by gently layering the cells in the wells with 50 µl of chilled 50% TCA (Trichloroacetic acid) for cell fixation. Plates were kept in refrigerator (4° C.) for 1 h. The plates were washed thoroughly with tap water for at least 5 times and air dried. For the assay, plates were stained with 50 µl of 0.4% SR-B for 20 min then washed with 1% acetic acid at least 5 times and air dried. Finally, the bound SR-B was eluted with 100 µl of Tris (10 mm, pH 10.5) for 10 min. Thereafter, the plates were shaken for 1 min using an automated shaker and the absorbance (O.D.) of each well was read in a micro plate reader (Thermo Electron Corporation, USA) at 540 nm with reference to 690 nm against blanks culture media without any cells.

Figure 14:
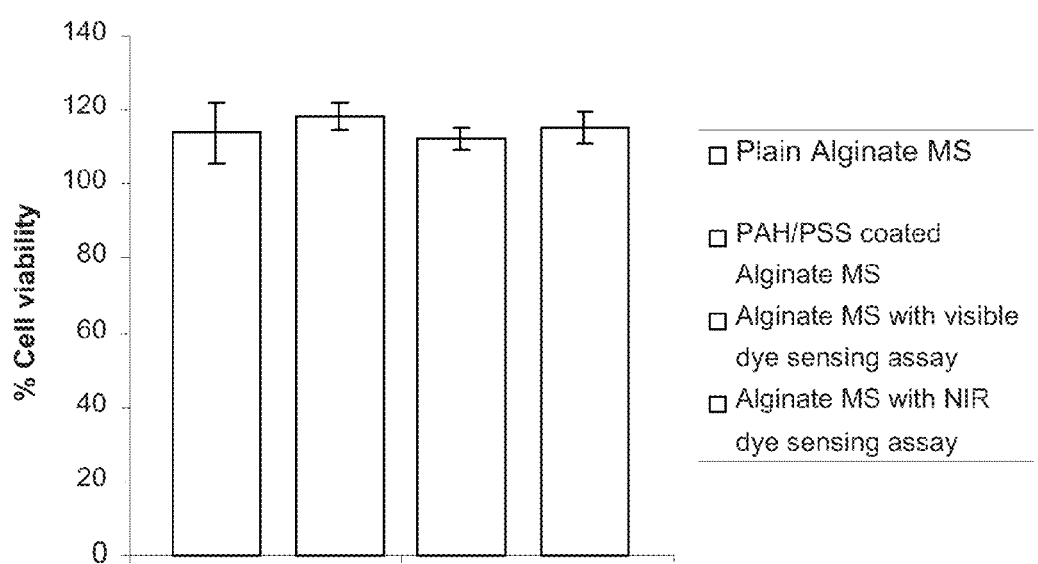
FIG. 14 is a bar graph illustrating cytotoxicity results of uncoated and polyelectrolyte coated fluorescent sensing assay loaded alginate microspheres. Mean±SD (n=3).

Cytotoxicity studies were carried out using L929 mouse fibroblast cell line on uncoated (plain microspheres) and polyelectrolyte coated microspheres containing the fluorescent glucose sensing and the results are depicted in FIG. 14. The % viability of the cells was approximately 100% with plain alginate microspheres (control), indicating that there was no cytotoxicity to cells. In case of [PAH/PSS]$_2$ coated alginate microspheres, the % viability of cells was again observed to be around 100%. Finally, the dissolved-core alginate templated microspheres loaded with the visible dye sensing assay and NIR dye sensing assay each separately also demonstrated 100% viability of cells. Therefore, it can be concluded from the cytotoxicity studies that the dissolved-core alginate templated microsphere glucose biosensors do not cause significant cell death to the L929 mouse fibroblast cell line, suggesting that the system has acceptable biocompatibility for use as glucose sensor implants.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. All references cited herein are incorporated by reference in their entireties and for all purposes to the same extent as if each individual publication, patent, or patent application was specifically and individually incorporated by reference in its entirety for all purposes.

What is claimed is:

1. An implantable glucose sensor, the sensor comprising:
    a population of alginate microspheres loaded with one or more anti-inflammatory agents, wherein the population is a mixture of uncoated and polyelectrolyte-coated alginate microspheres, and wherein the polyelectrolyte-coated alginate microspheres comprise an outer polyelectrolyte layer that is chemically or covalently cross-linked; and
    a population of dissolved core alginate microspheres incorporating one or more fluorophore-labeled glucose binding agents and one or more fluorophore-labeled glucose analogues.

2. The implantable glucose sensor of claim 1, wherein the dissolved core alginate microspheres have an average diameter of about 10 µm to about 20 µm.

3. The implantable glucose sensor of claim 1, wherein the population of alginate microspheres loaded with the one or more anti-inflammatory agents comprise from about 25% to about 90% polyelectrolyte coated microspheres.

4. The implantable glucose sensor of claim 3, wherein the population of alginate microspheres loaded with the one or more anti-inflammatory agents comprise about 75% polyelectrolyte coated microspheres and about 25% uncoated microspheres.

5. The implantable glucose sensor of claim 1, wherein the fluorophore on the one or more fluorophore-labeled glucose binding agents and the fluorophore on the one or more fluorophore-labeled glucose analogues form a FRET pair.

6. The implantable glucose sensor of claim 1, wherein the glucose binding agent is selected from the group consisting of: apo-glucose oxidase, Concanavalin A, and glucose binding protein.

7. The implantable glucose sensor of claim 1, wherein the one or more glucose analogues is selected from the group consisting of dextran amino, dextran, and β-cyclodextrin.

8. The implantable glucose sensor of claim 1, wherein the one or more anti-inflammatory agents are selected from the group consisting of: dexamethasone, hydrocortisone, cortisone acetate, prednisone, prednisolone, methylprednisolone, betamethasone, triamcinolone, diclofenac, ibuprofen, naproxen, and celecoxib.

9. The implantable glucose sensor of claim 1, wherein the polyelectrolyte comprise at least one bilayer of a polycation and a polyanion.

10. The implantable glucose sensor of claim 9, wherein the polycation is selected from the group consisting of: poly (allylamine hydrochloride) (PAH) and poly(diallyldimethylammonium chloride) (PDDA).

11. The implantable glucose sensor of claim 9, wherein the polyanion is selected from the group consisting of: poly(styrene sulfonate) (PSS) and poly(acrylic acid) (PAA).

12. The implantable glucose sensor of claim 9, wherein the at least one bilayer comprises a polyelectrolyte pair selected from the group consisting of: PAH/PSS, PDDA/PSS, PAH/PAA and cross-linked PAA/PAH.

13. The implantable glucose sensor of claim 1, wherein the alginate microspheres loaded with the one or more anti-inflammatory agents comprise from about 25% to about 90% by weight of the implantable glucose sensor and the dissolved core alginate microspheres comprise from about 50% to about 80% by weight of the implantable glucose sensor.

14. The implantable glucose sensor of claim 1, wherein the dissolved core alginate microspheres further comprise a reference fluorophore in a polyelectrolyte coating.

15. The implantable glucose sensor of claim 14, wherein the reference fluorophore is AF-750 tagged to a PAH polyelectrolyte.

16. A method for monitoring the blood glucose of a subject, the method comprising:
    detecting a fluorescence emission from an implanted glucose sensor, wherein the implanted glucose sensor comprises a population of alginate microspheres loaded with one or more anti-inflammatory agents, wherein the population is a mixture of uncoated and polyelectrolyte-coated alginate microspheres, and wherein the polyelectrolyte-coated alginate microspheres comprise an outer polyelectrolyte layer that is chemically or covalently cross-linked; and a population of dissolved core alginate microspheres incorporating one or more fluorophore-labeled glucose binding agents and one or more fluorophore-labeled glucose analogues;
    wherein the change in intensity of the fluorescence emission compared to a reference fluorescence is correlated to the blood glucose level of the subject.

17. The method of claim 16, further comprising detecting the fluorescence emission of the reference fluorophore.

18. The method of claim 16, wherein a ratio of the fluorescence emission from the one or more fluorophore-labeled glucose analogue compared to the fluorescence emission from the one or more fluorophore-labeled glucose binding agents is correlated to the blood glucose level of the subject.

19. The method of claim 17, wherein a ratio of the fluorescence emission from the one or more fluorophore-labeled glucose binding agents compared to the fluorescence emission of the reference fluorophore is correlated to the blood glucose level of the subject.

20. A kit for monitoring the blood glucose of a subject, the kit comprising:
    a population of alginate microspheres loaded with one or more anti-inflammatory agents, wherein the population is a mixture of uncoated and polyelectrolyte-coated alginate microspheres, wherein the polyelectrolyte-coated alginate microspheres comprise an outer polyelectrolyte layer that is chemically or covalently cross-linked;
    a population of dissolved core alginate microspheres incorporating one or more fluorophore-labeled glucose binding agents and one or more fluorophore-labeled glucose analogues; and
    optical instrumentation for detecting fluorescence emission from the one or more fluorophore-labeled glucose binding agents.

* * * * *

UNITED STATES PATENT AND TRADEMARK OFFICE
CERTIFICATE OF CORRECTION

Page 1 of 2

PATENT NO. : 8,916,136 B2
APPLICATION NO. : 12/819868
DATED : December 23, 2014
INVENTOR(S) : Srivastava et al.

It is certified that error appears in the above-identified patent and that said Letters Patent is hereby corrected as shown below:

On the Title Page, item (56), under "OTHER PUBLICATIONS", in Column 2, Line 15, delete "Med." and insert -- Med., --, therefor.

On the Title Page, item (56), under "OTHER PUBLICATIONS", in Column 2, Line 22, delete "rnicrocapsules" and insert -- microcapsules --, therefor.

On Page 2, item (56), under "OTHER PUBLICATIONS", in Column 1, Line 21, delete "Russell." and insert -- Russell, --, therefor.

On Page 2, item (56), under "OTHER PUBLICATIONS", in Column 1, Line 22, delete "poly)ethylene" and insert -- poly(ethylene --, therefor.

In the drawings:

In Fig. 13, Sheet 10 of 10, delete " 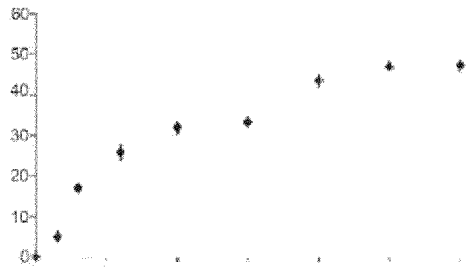 " and insert -- 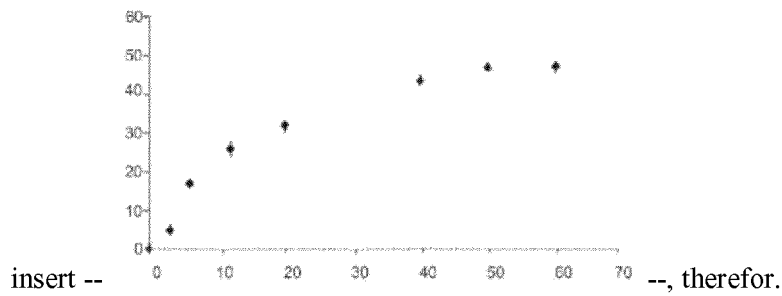 --, therefor.

Signed and Sealed this
First Day of March, 2016

Michelle K. Lee
*Director of the United States Patent and Trademark Office*

CERTIFICATE OF CORRECTION (continued)
U.S. Pat. No. 8,916,136 B2

In the specification:

In Column 13, Line 64, delete "shaking" and insert -- shaking. --, therefor.

In Column 15, Line 2, delete "-SO$_2$"" and insert -- -SO$_2$ --, therefor.

In Column 17, Line 62, delete "isofluorane" and insert -- isoflurane --, therefor.

In Column 20, Line 28, delete "NAPS" and insert -- NAP5 --, therefor.

In Column 20, Line 40, delete "Concavalin-A" and insert -- Concanavalin-A --, therefor.

In Column 21, Line 60, delete "cross-linking" and insert -- cross-linking. --, therefor.